(12) United States Patent
Chung

(10) Patent No.: US 9,370,524 B2
(45) Date of Patent: *Jun. 21, 2016

(54) METHOD FOR REDUCING RADIATION-INDUCED NORMAL TISSUE DAMAGE

(75) Inventor: Yih-Lin Chung, Taipei (TW)

(73) Assignee: Sunny Pharmatech Inc., New Taipei (TW)

(*) Notice: Subject to any disclaimer, the term of this patent is extended or adjusted under 35 U.S.C. 154(b) by 1474 days.

This patent is subject to a terminal disclaimer.

(21) Appl. No.: 10/798,119

(22) Filed: Mar. 11, 2004

(65) Prior Publication Data

US 2005/0272644 A1 Dec. 8, 2005

Related U.S. Application Data

(63) Continuation-in-part of application No. 10/205,738, filed on Jul. 25, 2002, now Pat. No. 6,809,118.

(51) Int. Cl.

| A61K 31/545 | (2006.01) |
| A61K 31/075 | (2006.01) |
| A61K 31/165 | (2006.01) |
| A61K 31/19  | (2006.01) |
| A61K 38/15  | (2006.01) |

(Continued)

(52) U.S. Cl.
CPC .............. *A61K 31/545* (2013.01); *A61K 31/075* (2013.01); *A61K 31/165* (2013.01); *A61K 31/19* (2013.01); *A61K 38/15* (2013.01); *A61K 9/06* (2013.01); *A61K 9/127* (2013.01)

(58) Field of Classification Search
None
See application file for complete search history.

(56) References Cited

U.S. PATENT DOCUMENTS

| 5,281,623 A | 1/1994 | Clemens et al. |
| 5,430,064 A | 7/1995 | Hirsch et al. |

(Continued)

FOREIGN PATENT DOCUMENTS

| WO | WO 98/29109 | 9/1998 |
| WO | WO 01/17514 | 3/2001 |

OTHER PUBLICATIONS

Shufeng, Z., et al., 5,6-Dimethylxanthenone-4-acetic acid (DMXAA): A New Biological Response Modifier for Cancer Therapy, Investigational New Drugs, vol. 20, 2002, pp. 281-295.*

(Continued)

*Primary Examiner* — Anna Pagonakis
(74) *Attorney, Agent, or Firm* — Cesari and McKenna LLP

(57) ABSTRACT

The present invention provides compositions and methods for increasing therapeutic gain in radiotherapy and chemotherapy for proliferating malignant or nonmalignant disease to produce high probability of tumor control with low frequency of sequelae of therapy by administering a therapeutically effective amount of a histone deacetylase inhibitor. The compounds are capable of simultaneously stimulating the epithelium regrowth, inhibiting the fibroblast proliferation, decreasing the collagen deposit, suppressing the fibrogenic growth factor, subsiding the proinflammatory cytokine and modulating the expression of cell cycle genes, tumor suppressors and oncogenes, and are useful to increase the therapeutic gain in radiotherapy and chemotherapy, which results in decrease of skin swelling and inflammation, promotion of epithelium healing in mucosa and dermis, decrease of xerostomia, prevention/reduction of severity of plantar-palmar syndrome, prevention of tissue fibrosis, ulceration, necrosis and tumorigenesis, and increase of tumor growth inhibition and tumor therapy effectiveness.

5 Claims, 24 Drawing Sheets

(51) Int. Cl.
*A61K 9/06* (2006.01)
*A61K 9/127* (2006.01)

(56) References Cited

U.S. PATENT DOCUMENTS

| | | | |
|---|---|---|---|
| 5,605,930 | A | 2/1997 | Samid |
| 5,877,213 | A * | 3/1999 | Samid .................. 514/568 |
| 5,993,845 | A | 11/1999 | Geerts et al. |
| 6,124,495 | A | 9/2000 | Neiss et al. |
| 6,225,294 | B1 | 5/2001 | Daifotis et al. |
| 6,242,012 | B1 * | 6/2001 | Newmark et al. .............. 424/756 |
| 6,313,091 | B1 | 11/2001 | Wisniewski et al. |
| 6,403,555 | B1 | 6/2002 | Skov |
| 6,538,030 | B2 * | 3/2003 | Chung et al. .................. 514/570 |
| 6,548,479 | B1 | 4/2003 | Skov |
| 6,809,118 | B2 * | 10/2004 | Chung .................. 514/570 |
| 2001/0009922 | A1 | 7/2001 | Faller |
| 2001/0012513 | A1 | 8/2001 | Robl et al. |
| 2001/0021700 | A1 * | 9/2001 | Moore et al. .................. 514/44 |
| 2002/0055542 | A1 * | 5/2002 | Chung et al. .................. 514/570 |
| 2002/0183388 | A1 | 12/2002 | Gudas et al. .................. 514/570 |
| 2003/0082666 | A1 | 5/2003 | Kammer et al. |
| 2003/0114525 | A1 | 6/2003 | Kammer et al. |
| 2003/0134865 | A1 | 7/2003 | Adcock et al. |
| 2003/0147926 | A1 | 8/2003 | Ebert et al. |
| 2005/0171206 | A1 | 8/2005 | Brahe et al. |
| 2006/0251689 | A1 | 11/2006 | Weidner |

OTHER PUBLICATIONS

See generally, Danesi, Romano et al., "Pharmacogenetic Determinants of Anti-Cancer Drug Activity and Toxicity," TRENDS in Pharmacological Sciences, vol. 22, No. 8, pp. 420-426 and p. 420, the abstract, particularly (Aug. 2001).*
Goldman, Lee, et al, Cecil Textbook of Medicine, vol. 1, pp. 1061-1074, 21st ed. (2000).*
"Structure-Activity Relationship and Drug Design." Remington's Pharmaceutical Sciences (Sixteenth Edition). Mack Publishing. 1980. pages 420-425.*
Berge et al. "Pharmaceutical Salts." Journal of Pharmaceutical Sciences, 66(1), 1977; 1-19.*
Ruescher et al. The impact of mucositis on alpha-hemolytic streptococcal infection in patients undergoing autologous bone marrow transplantation for hematologic malignancies. Cancer, vol. 82, Issue 11, Published online Oct. 31, 2000.*
Ruescher et al. The impact of mucositis on alpha-hemolytic streptococcal infection in patients undergoing autologous bone marrow transplantation for hematologic malignancies. Cancer, vol. 82, Issue 11, Article first published online Oct. 31, 2000.*
ADR news, Phenytoin. Stevens-Johnson syndrome: case report, Serious Reactions (ADR news), Feb. 22, 1996, ADISNEWS. See: abstract.
Merck Index, Ninth Edition, 1976, pp. 137 and 1273.
U.S. Appl. No. 09/938,926, Chung et al.
Chung et al. "Antitumor histone deacetylase inhibitors suppress cutaneous radiation syndrome: implications for increasing therapeutic gain in cancer radiotherapy" Molecular Cancer Therapeutics 2004;3(3):317-325.
Mishra et al., "Histone Deacetylase Inhibitor Trichostatin A as a Strong Candidate for Treatment of Systemic Lupus Erythematosus," FASEB Journal, 5:A1214, Mar. 2001.
Mishra et al., "Trichostatin A Reverses Skewed Expression of CD154, Interleukin-10, and Interferon-Gamma Gene and Protein Expression in Lupus T Cells," Proceedings of the National Academy of Sciences of USA 98(5):2628-2633, (2001).
Richon et al., "Histone Deacetylase Inhibitor Selectively Induces P21 WAF1 Expression and Gene-Associated Histone Acetylation," PNAS, 97(18):10014-10019, Aug. 28, (2000).
Witt et al., "Induction of Fetal Hemoglobin Expression by the Histone Deacetylase Inhibitor Apicdin," Blood 101(5), Mar. 1, (2003).
www.merriam-webster.com/dictionary/prevent, Nov. 13, 2007.
Goldring et al., Mechanisms of Bone Loss in Inflammatory Arthritis: Diagnosis and Therapeutic Implications, Arthritis Res 2000, 2:33-37.
Stoilov et al.,"Inhibition of Repair of X-ray-induced DNA Double-Strand Breaks in Human Lymphocytes Exposed to Sodium Butyrate," *International Journal of Radiation Biology* vol. 76, No. 11, pp. 1485-1491 (2000).
Miller et al., "Modulation of Radiation Response of Human Tumour Cells by the Differentiation Inducers, Phenylacetate and Phenylbutyrate," *International Journal of Radiation Biology* vol. 72, No. 2, pp. 211-218 (1997).
Saunders et al., "Histone Deacetylase Inhibitors as Potential Anti-Skin Cancer Agents," *Cancer Research* vol. 59, pp. 399-404 (1999).

* cited by examiner 1  2  3  4
Acetylated H3 
Coomassie stain 
FIG. 1B

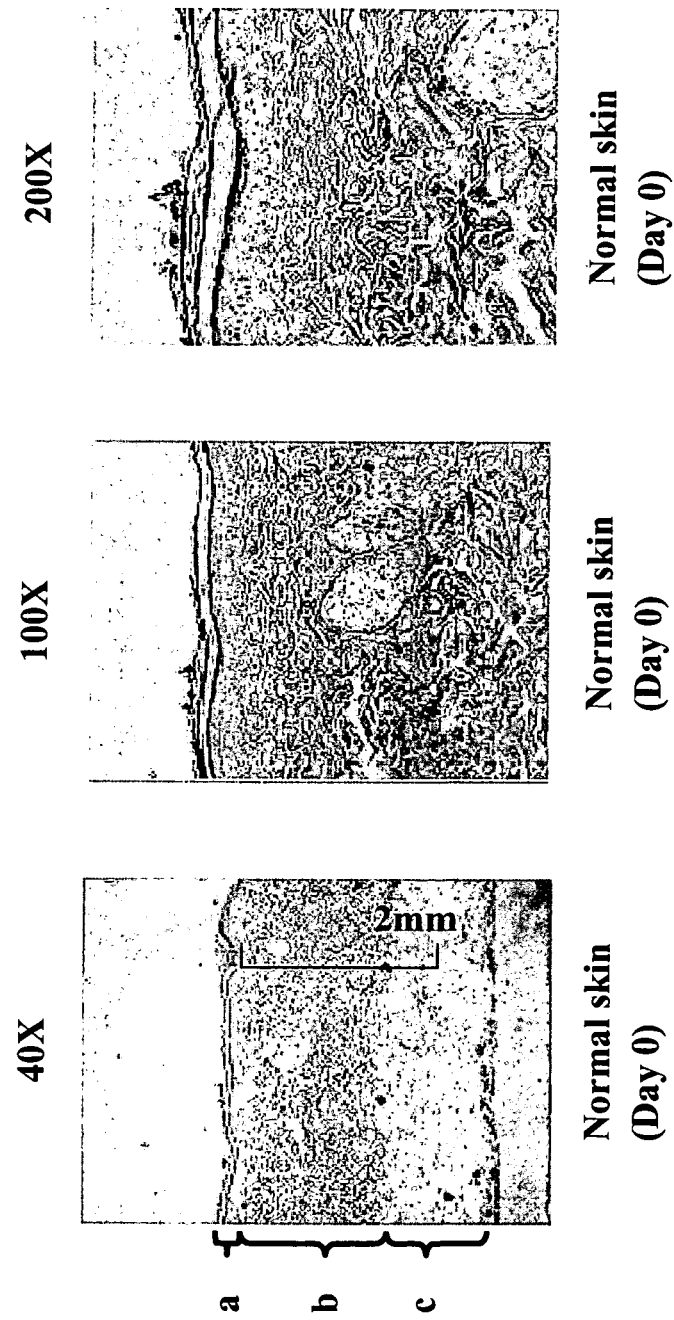

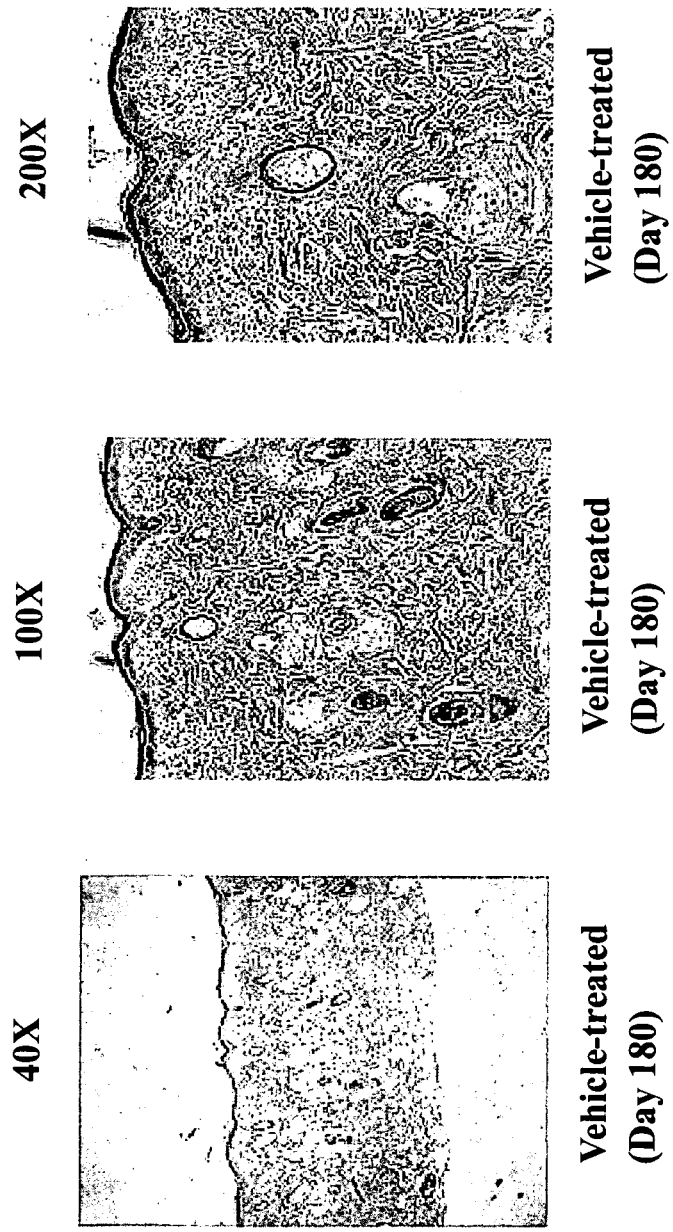
FIG. 3G  Vehicle-treated (Day 180)
FIG. 3H  Vehicle-treated (Day 180)
FIG. 3I  Vehicle-treated (Day 180)

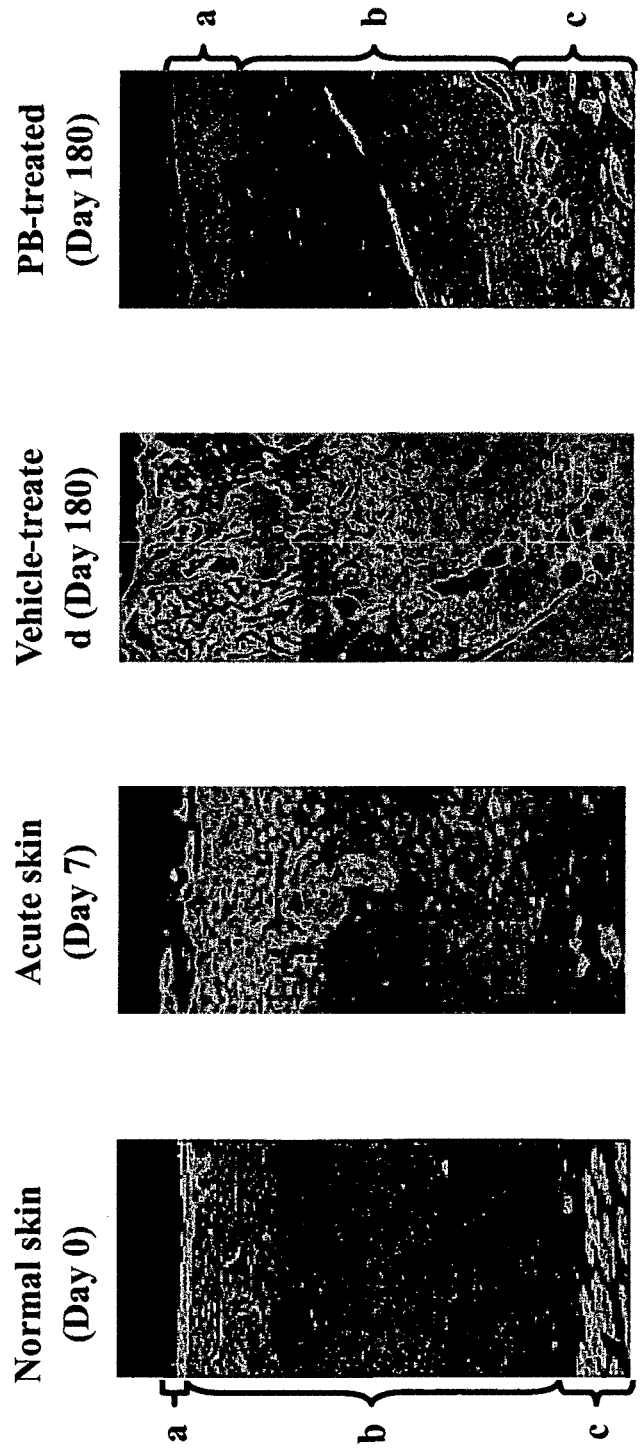

METHOD FOR REDUCING RADIATION-INDUCED NORMAL TISSUE DAMAGE

This application is a continuation in part of U.S. patent application Ser. No. 10/205,738.

BACKGROUND OF THE INVENTION

1. Field of the Invention

The present invention relates to the treatment of radiation- and/or chemotherapy-induced injuries. More particularly, the present invention relates to a method and pharmaceutical composition for increasing therapeutic gain in radiotherapy and chemotherapy.

2. Description of the Related Art

Radiotherapy with or without concurrent or sequential chemotherapy is an effective modality for head and neck, breast, skin, anogenital cancers, and certain nonmalignant diseases such as keloid, desmoid tumor, hemangioma, arteriovenous malformation, and histocytosis X. However, the therapeutic benefit is limited by radiation- and chemotherapy-induced mucosal epithelium injuries and cutaneous radiation syndrome (CRS), which include acute reactions of tissue swelling, mucositis, dermatitis, desquamation, and ulceration, and long-term effects of tissue/skin fibrosis, necrosis, and the development of life-threatening sequelae of sarcoma, squamous and basal cell carcinoma (Peter, R. U. The cutaneous radiation syndrome. Advances in the treatment of radiation injuries, pp. 237-240. Oxford: Elsevier, 1996). In fact, the skin is affected in every form of the external radiotherapy of internal organs, and mucositis can occur in the oral cavity, esophagus, gastrointestinal tract, bladder, vagina, rectum, lung, nasal cavity, ear and orbita as a side effect of chemotherapy and radiotherapy. The application of steroidal or non-steroidal anti-inflammatories is the most common treatment for radiation and chemotherapy-induced tissue injury, yet the results are unsatisfactory. An approach to selectively reduce skin morbidity without compromising the tumor-killing effects of radiotherapy and chemotherapy is a long-sought goal in radiation and medical oncology.

Drugs that have previously been tested in the management of radiation- and chemotherapy-induced damage include antioxidants (vitamin E and superoxide dismutase), anti-inflammatory agents (corticosteroids, colchicines, D-penicillamine, and TNF-α antagonist antibodies), and anti-fibrogenic agents (interferon, TGF-β antagonist, and angiotensin-converting enzyme inhibitors). None of these are able to simultaneously ameliorate acute dermatitis and mucositis, prevent the occurrence of fibrosis, and reduce late tumorigenesis; moreover, toxicities, side effects, tumor protection possibilities, and a lack of antitumor effects are troublesome.

SUMMARY OF THE INVENTION

The present invention provides a method and pharmaceutical composition for increasing therapeutic gain in radiotherapy and/or chemotherapy by producing the high probability of tumor control with a low frequency of complications or sequelae of therapy in a subject in need thereof. The pharmaceutical composition comprises a treatment effective amount of a histone hyperacetylating agent and a pharmaceutically acceptable carrier or a pharmaceutically acceptable salt thereof. The method comprises administrating the pharmaceutical composition to a subject in need.

The purpose of the method and pharmaceutical composition of the present invention includes simultaneously (1) enhancing the suppression of tumor or proliferating cell growth in a host in need of radiotherapy and/or chemotherapy, and (2) preventing the onset of or ameliorating the radiation- and/or chemotherapy-induced complications or sequelae of mucositis, dermatitis, ulceration, fibrosis, xerostomia, plantar-palmar syndrome, and tumorigenesis.

According to the present invention, it was surprisingly found that the pharmaceutical composition containing the histone deacetylase inhibitor reduced radiation-induced normal tissue fibrosis, promoted radiation-induced wound healing in mucositis and dermatitis, prevented chemotherapy-induced tissue necrosis, prevented radiation-related tumorigenesis, exhibited direct antitumor effect, enhanced tumor radiosensitization, and synergistically inhibited tumor cell growth with radiotherapy and other anti-cancer agents.

The compounds of the present invention can be administered intravenously, enterally, parentally, intramuscularly, intranasally, subcutaneously, topically or orally. The dosage amounts are based on the effective concentration observed in vitro and in vivo studies. The varied and efficacious utility of the compounds of the present invention is further illustrated by the discovery that they may also be administered concomitantly or in combination with a cytokine, an interleukin, an anti-cancer agent or an anti-neoplastic agent, an anti-angiogenesis agent, a chemotherapeutic agent, an antibody, a conjugated antibody, an immune stimulant, an antibiotic, retinoic acid, a tyrosine kinase inhibitor, a hormone antagonist or a growth stimulant.

BRIEF DESCRIPTION OF THE DRAWINGS

The present invention will be more fully understood and further advantages will become apparent when reference is made to the following description of the invention and the accompanying drawings in which:

FIG. 1B shows western blot analysis for acetylated H3 in the irradiated skin (40 Gy single fraction) treated with or without phenylbutyrate cream (PB) for 6 hours after irradiation. 1, Normal skin without irradiation; 2, irradiated skin without any treatment; 3, irradiated skin treated with the vehicle; 4, irradiated skin treated with the 1% PB cream.

FIG. 1C shows normal skin without irradiation; FIG. 1D shows irradiated skin without any treatment; FIG. 1E shows irradiated skin treated with the vehicle; and FIG. 1F shows irradiated skin treated with the 1% PB cream.

FIGS. 3A-3L are the H&E histology photographs showing that the topical histone deacetylase inhibitors have effects on suppressing the radiation-induced skin damage. 3A, 3D, 3G, and 3J are H&E histology at 40× field; 3B, 3E, 3H, and 3K are H&E histology at 100× field; 3C, 3F, 3I, and 3L are H&E histology at 200× field. FIGS. 3A-3C are of normal skin. FIGS. 3D-3F are of acute reaction on Day 7 after irradiation, showing subepithelial swelling (white arrow). FIGS. 3G-3I are of the vehicle group on Day 180, showing thinner epithelium, subepithelium swelling, increased vessel and skin appendage density, and thick dermis with more collagen deposit. The black arrowheads indicate that the subcutaneous fat layer in the vehicle group was replaced by fibrous tissues and appendages. FIGS. 3J-3L are of the histone deacetylase inhibitor treated group on Day 180, showing thicker epidermis with 10-30 cell layers (black arrow), less subepithelial swelling, a thinner dermis with less collagen deposition, and few skin appendages.

FIG. 4A shows the changes of TGF-β1 levels after irradiation treated with or without the topical phenylbutyrate (PB). FIG. 4B shows the changes of TGF-β2 levels after irradiation treated with or without the topical phenylbutyrate (PB). FIG. 4C shows the changes of TGF-β3 levels after irradiation treated with or without the topical phenylbutyrate (PB). FIG. 4D shows the changes of TNF-α levels after irradiation treated with or without the topical phenylbutyrate (PB).

FIGS. 5A-5D are photographs of immunofluorescence with the anti-TGF-beta 1,2 antibodies showing that the expression of TGF-beta, a fibrogenic growth factor, was suppressed by the histone deacetylase inhibitor in example 4. FIG. 5A is of normal skin stained with TGF-beta. FIG. 5B is a picture of acute dermatitis on Day 7 after irradiation without any drug treatment, showing that TGF-beta was up-regulated. FIG. 5C is of the vehicle group on Day 180 after irradiation, showing that the expression of TGF-beta was increased with time, persistent and highly expressed in fibrogenic skin both in keratinocytes of the epidermis and in myofibroblasts of the dermis. FIG. 5D is of the PB treated-group on Day 180 after irradiation, showing that the topical PB suppressed the TGF-beta expression effectively, which correlates well with less collagen fiber accumulation in dermis and more cell layers in epithelium since TGF-beta triggers fibroblast proliferation but inhibits epithelial cell growth.

FIG. 6A is of normal skin for TNF-alpha staining. FIG. 6B is of the PB treated-group on Day 270 after irradiation, showing that the histone deacetylase inhibitor suppressed the TNF-α expression effectively, which correlates well with less inflammatory cell infiltration and no chronic ulceration. FIG. 6C is an irradiated skin treated with Vaseline, showing that TNF-α was up-regulated in the subcutaneous tissue with ulcerations on Day 270 (the arrow indicates the necrotic wound). FIG. 6D is an irradiated skin treated with vehicle, showing that TNF-α was up-regulated in the subcutaneous tissue with heavy inflammatory cell infiltrates on Day 270.

FIG. 8A shows time-course analysis of the up-regulated levels of p21Cip1 protein, a cell-cycle inhibitor, in BNL 1MEA7R.1 and CT-26 carcinoma cells during treatment with 4 mM PB. FIGs. BB-8C shows the growth inhibition curve. FIGS. 8D-8F shows the tumor growth inhibition in vivo; FIG. 8D shows an initial tumor size of 1MEA7R.1 beneath the skin about 0.5 cm in dimension before treatment; FIG. 8E is of a placebo- or vehicle-treated tumor at week 4; FIG. 8F is of a PB-treated tumor at week 4.

FIG. 11A shows TSA 1 nM for 48 hours up-regulated the EBV thymidine kinase activity in EBV-positive Daudi cells. FIG. 11B shows that the combination of TSA, GCV, and radiation produces maximal death of EBV-positive cells. Bars represent the mean of three different experiments performed in triplicate.

DETAILED DESCRIPTION OF THE INVENTION

Figure 1A:
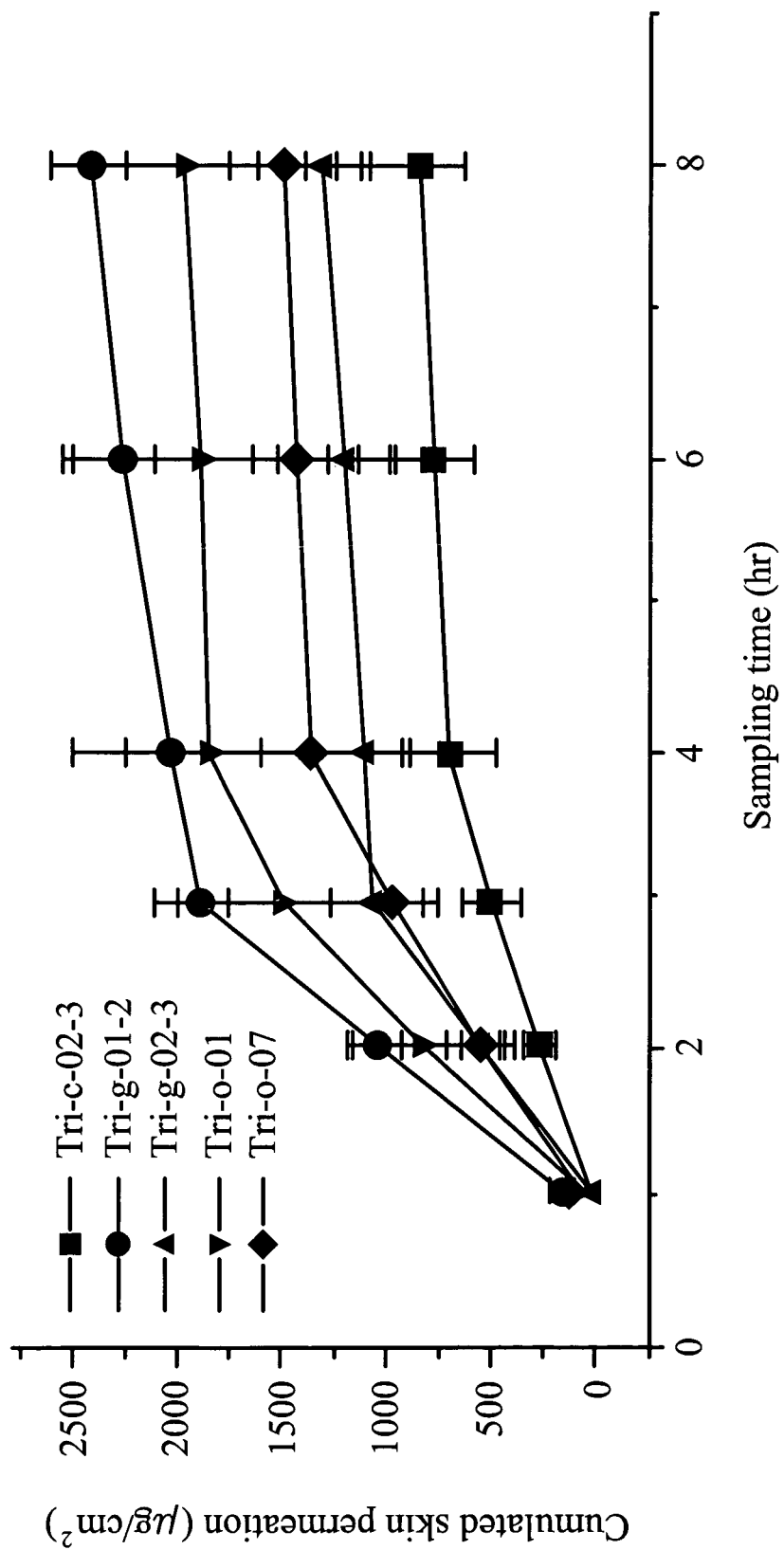
FIG. 1A shows pharmacokinetic studies of delivery of different PB formulations through the skin.
Figure 1C:
FIGS. 1C-1F show immunofluorescence staining of acetylated H3 in the irradiated skin treated with or without the phenylbutyrate cream (PB) for 6 hours after irradiation.
Figure 1D:
Figure 1E:
Figure 1F:

After radiation and/or chemotherapy agents induce injuries, the release of cytokines (such as tumor necrosis factor (TNF-α)) and growth factors (such as transforming growth factor (TGF-β)) in affected tissues perpetuates and augments the inflammatory response, while promoting fibroblast recruitment and proliferation but inhibiting epithelial cell growth (Hill et al, Int. J. Radiat. Oncol. Biol. Phys., 49: 353-365, 2001; Seong et al, Int. J. Radiat. Oncol. Biol. Phys., 46: 639-643, 2000; Wang et al, Am. J. Pathol., 153: 1531-1540, 1998; Fedorocko et al, Int. J. Radiat. Biol., 78: 305-313, 2002; Martin et al, Int. J. Radiat. Oncol. Biol. Phys., 47: 277-290, 2000; Randall et al, Int. J. Radiat. Biol., 70: 351-360, 1996; Border et al, N. Engl. J. Med., 331: 1286-1292, 1994; Singer et al, N. Engl. J. Med., 341: 738-746, 1999). Especially, the amplified injury response to radiation by the persistent secretion of TNF-α and TGF-β from epithelial, endothelial, and connective tissue cells, which is possibly caused by a modification in the genetic programming of cell differentiation and proliferation, leads to the histological modifications that characterize CRS (Zhou et al, Int. J. Radiat. Biol., 77: 763-772, 2001; Skwarchuk et al, Int. J. Radiat. Oncol. Biol. Phys., 42: 169-178, 1998; Sivan et al, Int. J. Radiat. Oncol. Biol. Phys., 53: 385-393, 2002; Delanian et al, Radiother. Oncol., 47: 255-261, 1998). The chronic activation of TGF-β pathway also stimulates late tumorigenesis (Wieser et al, Curr. Opin. Oncol., 13: 70-77, 2001; Massague et al, Cell, 103: 295-309, 2000). Thus, CRS and radiation-induced carcinogenesis could be regarded as a genetic disorder of the wound healing process after radiation exposure.

A class compound of gene modulators, histone deacetylase (HDAC) inhibitors, activates and represses a subset of genes by remodeling the chromatin structure via the altered status in histone acetylation (Marks et al, J. Natl. Cancer Inst., 92: 1210-1216, 2000; Kramer et al, Trends Endocrinol. Metab., 12: 294-300, 2001). Histone hyperacetylation results in the up-regulation of cell-cycle inhibitors (p21Cip1, p27Kip1, and p16INK4), the down-regulation of oncogenes (Myc and Bcl-2), the repression of inflammatory cytokines (interleukin (IL)-1, IL-8, TNF-α, and TGF-β), or no change (GAPDH and γ-actin)(Lagger et al, EMBO J., 21: 2672-2681, 2002; Richon et al, Clin. Cancer Res., 8: 662-667, 2002; Richon et al, Proc. Natl. Acad. Sci. USA., 97: 10014-10019, 2000; Van Lint et al, Gene Expr., 5: 245-243, 1996; Huang et al, Cytokine, 9: 27-36, 1997; Mishra et al, Proc. Natl. Acad. Sci. USA., 98:

2628-2633, 2001; Stockhammer et al, J. Neurosurg., 83: 672-681, 1995; Segain et al, Gut, 47: 397-403, 2000; Leoni et al, Proc. Natl. Acad. Sci. USA, 99: 2995-3000, 2002). In addition to inducing histone hyperacetylation, HDAC inhibitors also induce hyperacetylation of nonhistone proteins such as ribosomal S3, p53 or the Rel-A subunit of NF-κB, modulate protein kinase C (PKC) activity, inhibit protein isoprenylation, decrease DNA methylation, and bind to nuclear receptors (Webb et al, J. Biol. Chem., 274: 14280-14287, 1999; Chen et al, Science, 293: 1653-1657, 2001). HDAC inhibitors have exhibited properties in inducing cell-cycle arrest, cell differentiation, and apoptotic cell death in tumor cells and in decreasing inflammation and fibrosis in inflammatory diseases (Warrell et al, J. Natl. Cancer Inst., 90: 1621-1625, 1998; Vigushin et al, Clin. Cancer Res., 7: 971-976, 2001; Saunders et al, Cancer Res., 59: 399-404, 1999; Gottlicher et al, EMBO J., 20: 6969-6978, 2001; Rombouts et al, Acta Gastroenterol. Belg., 64: 239-246, 2001). Although the effects of HDAC inhibitors induce bulk histone acetylation, they result in apoptotic cell death, terminal differentiation, and growth arrest in tumor cells but no toxicity in normal cells (Garber et al, J. Natl. Cancer Inst., 94: 793-795, 2002). In addition, the modulation of chromatin conformation by HDAC inhibitors can further radiosensitize tumors whose cells are intrinsically radioresistant, and also sensitize tumor cells to chemotherapy (Ferrandina et al, Oncol. Res., 12: 429-440, 2001; Miller et al, Int. J. Radiat. Biol., 72: 211-218, 1997; Biade et al, Int. J. Radiat. Biol., 77: 1033-1042, 2001).

Thus, on the basis of the abilities in simultaneously, coordinately, selectively, and epigenetically manipulating the expression of tumor suppressors, oncogenes, proinflammatory cytokines (TNF-α), and fibrogenic growth factors (TGF-β) by differentially remodeling the chromatins in normal and tumor cells, a pharmaceutical composition comprising the HDAC inhibitor may provide an effective treatment not only to decrease radiation- and/or chemotherapy-induced mucosa/skin damage but also to enhance anti-tumor effects to maximize the therapeutic effectiveness of radiotherapy and/or chemotherapy.

Active compounds used to carry out the present invention are, in general, histone hyperacetylating agents, such as histone deacetylase inhibitors. Numerous such compounds are known. See, e.g., P. Dulski, Histone Deacetylase as Target for Antiprotozoal Agents, PCT Application WO 97/11366 (Mar. 27, 1997). Examples of such compounds include, but are not limited to:

A. Trichostatin A and its analogues such as: Trichostatin A (TSA); and Trichostatin C (Koghe et al. 1998. Biochem. Pharmacol. 56:1359-1364) (Trichostatin B has been isolated but not shown to be an HDAC inhibitor).

B. Peptides, such as: Oxamflatin [(2E)-5-[3-[(phenylsufonyl)aminol phenyl1]-pent-2-en-4-ynohydroxamic acid (Kim et al. Oncogene, 18:2461-2470 (1999)); Trapoxin A (TPX)—Cyclic Tetrapeptide (cyclo-(L-phenylalanyl-L-phenylalanyl-D-pipecolinyl-L-2-amino-8-oxo-9,10-epoxy-decanoyl)) (Kijima et al., J. Biol. Chem. 268, 22429-22435 (1993)); FR901228, Depsipeptide (Nakajima et al., Ex. Cell Res. 241, 126-133 (1998)); FR225497, Cyclic Tetrapeptide (H. Mori et al., PCT Application WO 00/08048 (Feb. 17, 2000)); Apicidin, Cyclic Tetrapeptide [cyclo(N—O-methyl-L-tryptophanyl-L-isoleucinyl-D-pipecoliny 1-L-2-amino-8-oxodecanoyl)] (Darkin-Rattray et al., Proc. Natl. Acad. Sci. USA 93, 13143-13147 (1996)); Apicidin 1a, Apicidin Ib, Apicidin Ic, Apicidin IIa, and Apicidin IIb (P. Dulski et al., PCT Application WO 97/11366); HC-Toxin, Cyclic Tetrapeptide (Bosch et al., Plant Cell 7, 1941-1950 (1995)); WF27082, Cyclic Tetrapeptide (PCT Application WO 98/48825); and chlamydocin (Bosch et al., supra).

C. Hydroxamic Acid-Based Hybrid Polar Compounds (HPCs), such as: Salicylihydroxamic Acid (SBHA) (Andrews et al., International J. Parasitology 30, 761-768 (2000)); Suberoylanilide Hydroxamic Acid (SAHA) (Richon et al., Proc. Natl. Acad. Sci. USA 95, 3003-3007 (1998)); Azelaic Bishydroxamic Acid (ABHA) (Andrews et al., supra); Azelaic-1-Hydroxamate-9-Anilide (AAHA) (Qiu et al., Mol. Biol. Cell 11, 2069-2083 (2000)); M-Carboxycinnamic Acid Bishydroxamide (CBHA) (Ricon et al., supra); 6-(3-Chlorophenylureido)carpoic Hydroxamic Acid (3-Cl-UCHA) (Richon et al., supra); MW2796 (Andrews et al., supra); and MW2996 (Andrews et al., supra). Note that analogs not effective as HDAC Inhibitors are: Hexamethylene bisacetamide (HBMA) (Richon et al. 1998, PNAS, 95:3003-3007); and Diethyl bis(pentamethylene-N,N-dimethylcarboxami-de) malonate (EMBA) (Richon et al. 1998, PNAS, 95:3003-3007).

D. Short Chain Fatty Acid (SCFA) Compounds, such as: Sodium Butyrate (Cousens et al., J. Biol. Chem. 254, 1716-1723 (1979)); Isovalerate (McBain et al., Biochem. Pharm. 53:1357-1368 (1997)); Valproic acid; Valerate (McBain et al., supra); 4-Phenylbutyrate (4-PBA) (Lea and Tulsyan, Anticancer Research, 15, 879-873 (1995)); Phenylbutyrate (PB) (Wang et al., Cancer Research, 59, 2766-2799 (1999)); Propionate (McBain et al., supra); Butrymide (Lea and Tulsyan, supra); Isobutyramide (Lea and Tulsyan, supra); Phenylacetate (Lea and Tulsyan, supra); 3-Bromopropionate (Lea and Tulsyan, supra); and Tributyrin (Guan et al., Cancer Research, 60, 749-755 (2000)).

E. Benzamide derivatives, such as: MS-27-275 [N-(2-aminophenyl)-4-[N-(pyridin-3-yl-methoxycarbonyl)aminomethyl]benzamide] (Saito et al., Proc. Natl. Acad. Sci. USA 96, 4592-4597 (1999)); and 3'-amino derivative of MS-27-275 (Saito et al., supra).

F. Other inhibitors, such as: Depudecin [its analogues (mono-MTM-depudecin and depudecin-bisether) do not inhibit HDAC] (Kwon et al. 1998. PNAS 95:3356-3361); and Scriptaid (Su et al. 2000 Cancer Research, 60:3137-3142).

The description in this application is in particular directed to valproic acid, trichostatin A, and phenylbutyrate for increasing therapeutic gain in radiotherapy and chemotherapy for proliferating malignant or nonmalignant disease to produce high probability of tumor control with low frequency of sequelae of therapy, as non-limiting examples and is not intended to limit the scope of the invention. Pharmaceutical formulations and the use of compounds of valproic acid, trichostatin A and phenylbutyrate are also disclosed.

In the course of experiments, valproic acid, trichostatin A and phenylbutyrate as histone deacetylase inhibitors were discovered to have strong effects on not only decreasing skin swelling, promotion of desquamation healing in mucositis and dermatitis, reduction of fibrosis, and prevention of tumorigenesis in irradiated tissue/skin but also inhibition of tumor cell growth, and enhancement of tumor radiosensitization.

The histone deacetylase inhibitor agents can be brought in the form of pharmaceutically acceptable salts. As such pharmaceutically acceptable salts may be used so long as they do not adversely affect the desired pharmacological effects of the compounds. The selection and production can be performed by those skilled in the art. Examples of pharmaceutically acceptable salts include alkali metal salts such as sodium salt or a potassium salt, alkaline earth metal salts such as calcium salt or a magnesium salt, salts with an organic base such as an ammonium salt, or a salt with an organic base such as a triethylamine salt or an ethanolamine salt.

The histone deacetylase inhibitor agents of the present invention may be administered orally or non-orally. In the case of oral administration, they may be administered in the form of soft and hard capsules, tablets, granules, powders, solutions, suspensions, mouthwash or the like. In the case of non-oral administration, they may be administered in the form of creams, ointments, gels, lotions, patches, suppositories, liposome formations, injection solution, drip infusion formulations, enema or the like whereby continued membrane absorption can be maintained in the form of solid, viscous liquid, or suspension. The selection of the method for the preparation of these formulations and the vehicles, disintegrators or suspending agents, can be readily made by those skilled in the art. The histone deacetylase inhibitor agents of the present invention may contain a further composition having anti-inflammatory or anti-tumor activities, in addition to valproic acid, trichostatin A, or phenylbutyrate, or other hyperacetylating agents and a pharmaceutically acceptable carrier or a pharmaceutically acceptable salt thereof.

As recognized by those skilled in the art, the effective doses vary depending on route of administration, excipient usage, and the possibility of co-use with other therapeutic treatments such as the use of a cytokine, an interleukin, an anti-cancer agent or an anti-neoplastic agent, an anti-angiogenesis agent, a chemotherapeutic agent, an antibody, a conjugated antibody, an immune stimulant, an antibiotic, retinoic acid, a tyrosine kinase inhibitor, a hormone antagonist or a growth stimulant. Effective amounts and treatment regimens for any particular subject (e.g., human, dog, or cat) will also depend upon a variety of other factors, including the activity of the specific compound employed, age, body weight, general health status, sex, diet, time of administration, rate of excretion, severity and course of the disease, and the patient's disposition to the disease, but are usually from 0.001% to 100% by weight of the composition irrespective of the manner of administration. Active compounds of the present invention may optionally be administered in conjunction with other compounds useful in increasing therapeutic gain in radiotherapy and/or chemotherapy for proliferative malignant or nommalignant disease. The other compounds may optionally be administered concurrently. As used herein, the word "concurrently" means sufficiently close in time to produce a combined effect (that is, concurrently may be simultaneously, or it may be two or more events occurring within a short time period before or after each other). As used herein, the administration of two or more compounds "concurrently" or "in combination" means that the two compounds are administered closely enough in time that the presence of one alters the biological effects of the other. The two compounds may be administered simultaneously or sequentially. Simultaneous administration may be carried out by mixing the compounds prior to administration, or by administering the compounds at the same point in time but at different anatomic sites or using different routes of administration.

As used herein, proliferating malignant disease comprises melanoma, Kaposi's sarcoma, osteosarcoma, neuroblastoma, rhabdomyosarcoma, Ewing's sarcoma, Soft tissue sarcoma, skin cancer, lymphoma, leukemia, breast cancer, germ cell tumor, primitive neuroectodermal tumor, brain glioma, brain meningioma, head and neck cancer, thyroid cancer, thymic cancer, cervical cancer, anus cancer, colorectal cancer, prostate cancer, lung cancer, hepatocellular carcinoma, cholangiocarcinoma, stomach cancer, pancreatic cancer, esophageal cancer, virus-associated tumors, and disease receiving bone marrow transplantation.

As used herein, the nonmalignant disease comprises pterygium, Graves' ophthalmopathy, orbital pseudotumor, macular degeneration, keloid, wart, keratoacanthoma, hemangioma, arteriovenous malformation, bursitis, tendinitis, desmoid tumor, Peyronie's disease, vascular stenosis, ameloblastoma, aneurysmal bone cyst, heterotopic bone formation, gynecomastia, ovarian castration, parotitis, eczema, atopic dermatitis, psoriasis, periarthritis humeroscapularis, epicondylitis, knee arthrosis, hydradenitis, panaritium, autoimmune inflammatory arthritis, histocytosis X, and disease from receiving organ transplantation.

In order that the invention described herein may be more readily understood, the following examples are set forth. It should be understood that these examples are for illustrative purposes only and are not to be construed as limiting this invention in any manner. All references cited herein are expressly incorporated by reference in their entirety.

EXAMPLE

Example 1

Various Topical Compositions-Oleaginous Ointment, Cream, and Gel

A. Preparation of an Oleaginous Ointment of Phenylbutyrate:

470 g of white petrolatum (Riedel-de Haen), 25 g of paraffin wax 50/52 (local supplier), and 5 g of 4-phenylbutyrate (Merck) were mixed in a beaker and heated at 70° C. to form a paste. The paste was stirred at 400 rpm for 1 hour, and then cooled at room temperature.

B. Preparation of an Oleaginous Ointment of Phenylbutyrate:

65 g of white petrolatum (Riedel-de Haen), 15 g of cetyl alcohol (Riedel-de Haen), 260 g of soft paraffin (Merck), 155 g of liquid paraffin (Merck), and 5 g of 4-phenylbutyrate (Merck) were mixed in a beaker and heated at 70° C. to form a paste. The paste was stirred at 400 rpm for 1 hour, and then cooled at room temperature.

C. Preparation of Cream of Phenylbutyrate:

Part I: 70 g of Tefose 63®, 20 g of Superpolystate®, 10 g of Coster 5000®, 15 g of Myriyol 318®, 15 g of Coster 5088®, and 15 g of GMS SE® (all commercially available from local supplier) were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), and 149.061 g of deionized water were mixed in a beaker and heated at 70° C.

The part II was slowly added into the part I and continually stirred at 400 rpm for 5 minutes to form a mixture. 2% Stabileze QM® (prepared by dissolving 2 g of Stabileze QM® in 98 g of deionized water, heating and stirring at 70° C. to form a paste, and cooling at room temperature) was added into the mixture and stirred for 5 minutes. The pH of the mixture was adjusted to 5.34 with 0.85% phosphoric acid (Merck), and stirred at 600 rpm for 20 minutes. The mixture was cooled at room temperature.

D. Preparation of Gel of Phenylbutyrate:

Part I: 10 g of Stabileze QM® and 232.035 g of deionized water were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), 232.035 g of deionized water, and 20 g of 10% NaOH were mixed in a beaker and heated at 70° C.

The part II was slowly added into the part I and continually stirred at 400 rpm for 20 minutes to form a mixture. The mixture was cooled at room temperature.

E. Preparation of Gel of Phenylbutyrate:

Part I: 10 g of Stabileze QM® and 380.5619 of deionized water were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), 83.5 g of 1,2-propandiol, and 20 g of 10% NaOH were mixed in a beaker and heated at 70° C.

The part II was slowly added into the part I and continually stirred at 400 rpm for 20 minutes to form a mixture. The mixture was cooled at room temperature.

F: Preparation of Sustained Release Formulations of Phenylbutyrate:

Two formulations were prepared according to the compositions listed in the Table 1.

TABLE 1

Compositions of two sustained release formulations

| Composition | No. of formulation | |
| --- | --- | --- |
| | Tri-s-04 | Tri-s-05 |
| PF-127 ® (BASF Inc.)* | 2 | 4 |
| Sodium carboxy-methylcellulose* | 12 | 12 |
| Deionized water | 82.8523 | 80.8523 |
| Sodium 4-phenylbutyrate | 1.1477 | 1.1477 |
| 85% phosphoric acid | 2 | 2 |
| pH | 5.93 | 6.01 |

*PF-127 ® is the base of the compositions, and sodium carboxymethylcellulose is a thickening agent.

G: Preparation of Liposomal Formulation of Phenylbutyrate:

In this liposomal formulation, egg phosphatidylcholine (EPC) and cholesterol were used in equi- or different-molar concentrations as primary lipid components. Various liposomes located with 4-phenylbutyrate were obtained by varying the lipid:phenylbutyrate ratio. Liposomes were prepared by thin film hydration, sized by membrane extrusion, and physically evaluated.

H: Preparation of Ointment of Trichostatin a:

472.5 g of white petrolatum (Riedel-de Haen), 27 g of paraffin wax 50/52 (local supplier), and 0.5 g of trichostatin A (sigma) were mixed in a beaker and heated at 70° C. to form a paste. The paste was stirred at 400 rpm for 1 hour, and then cooled at room temperature.

I. Preparation of an Oleaginous Ointment of Trichostatin A:

67.5 g of white petrolatum (Riedel-de Haen), 16 g of cetyl alcohol (Riedel-de Haen), 260.5 g of soft paraffin (Merck), 155.5 g of liquid paraffin (Merck), and 0.5 g of trichostatin A (sigma) were mixed in a beaker and heated at 70° C. to form a paste. The paste was stirred at 400 rpm for 1 hour, and then cooled at room temperature.

J. Preparation of Cream of Valproic Acid:

Part I: 70 g of Tefose 63®, 20 g of Superpolystate®, 10 g of Coster 5000®, 15 g of Myriyol 318®, 15 g of Coster 5088®, and 15 g of GMS SE® (all commercially available from local supplier) were mixed in a beaker and heated at 70° C.

Part II: 5.739 g of valproic acid (sigma), 0.125 g of methylparaben (Merck), 0.075 g of propylparaben (Merck), and 149.061 g of deionized water were mixed in a beaker and heated at 70° C.

The part II was slowly added into the part I and continually stirred at 400 rpm for 5 minutes to form a mixture. 2% Stabileze QM® (prepared by dissolving 2 g of Stabileze QM® in 98 g of deionized water, heating and stirring at 70° C. to form a paste, and cooling at room temperature) was added into the mixture and stirred for 5 minutes. The pH of the mixture was adjusted to 5.34 with 0.85% phosphoric acid (Merck), and stirred at 600 rpm for 20 minutes. The mixture was cooled at room temperature.

Example 2

Topical Phenylbutyrate (Pb) Treatment Induces Histone Hyperacetylation In Vivo

As shown in Table 2, several phenylbutyrate (PB) formulations were characterized.

TABLE 2

Formulation characteristics and pharmacokinetics parameters

| *PB (1%) Formulation | Tri-c-02-3 | Tri-g-01-2 | Tri-g-02-3 | Tri-o-01 | Tri-o-07 |
| --- | --- | --- | --- | --- | --- |
| Stability | Good | good | good | good | Poor |
| Shelf-life (mo) | 83.9 | 10.8 | 23.9 | 2.0 | 6.1 |
| Skin irritation | No | No | No | No | No |
| [1]Slope | 219.9 | 873.5 | 491.7 | 709.25 | 452.8 |
| [2]Y Intercept | −198.3 | −740.7 | −442 | −649.4 | −400.7 |
| [3]Retention time | 0.902 | 0.848 | 0.899 | 0.916 | 0.885 |
| [4]Constant | 1.18 | 1.26 | 1.19 | 1.16 | 1.21 |
| [5]Cs | 1.49 | 5.56 | 3.32 | 4.87 | 3.01 |
| [6]$\mu g/cm^2$ | 594.8 | 2222.2 | 1326.1 | 1948.2 | 1202.1 |
| [7]$mg/cm^3$ | 74 | 278 | 166 | 243 | 150 |

*c: cream; g: gel; o: ointment;
[1]slope, indicating the permeation amount of each drug through skin per hour ($\mu g/cm^2/hr$);
[2]Y intercept ($\mu g/cm^2$): a negative number indicating the potential permeation amount of each drug through skin, a positive number indicating that the sampling time is too long to obtain an accurate value;
[3]retention time, indicating the average time (hr) that drug spends to permeate skin;
[4]Constant ($\times 10^{-5}$ $cm^2/s$), the drug diffusion constant;
[5]Cs ($\times 10^5$ $mg/cm^3$), the drug concentration on skin surface;
[6]$\mu g/cm^2$, the average permeation amount of each drug through per $cm^2$ skin;
[7]$mg/cm^3$, the average concentration in skin.

Among the different formulations, the PB cream (Tri-c-02-3), which showed good stability, low rates of skin irritation, a long shelf life, and a high rate of skin penetration, was selected for testing (FIG. 1A). To determine what dosage of topical PB was suitable to treat irradiated skin, the amount of histone hyperacetylation in the nucleus was used as a marker to demonstrate the extent of drug penetration and to indicate whether the local drug concentration was enough to exert biological effects. Western blot analysis for acetylated histones in the irradiated skin 6 hours after irradiation (40 Gy single fraction) showed that the acetylated form of histone H3 was mildly increased in the control and vehicle-treated groups but was markedly increased with the topical treatment of 1% PB cream at a dose of 200 mg/irradiated skin surface given immediately after irradiation (FIG. 1B). The coomassie blue-stained gel sections demonstrate the equivalence of protein loading. Immunofluorescence staining further demonstrated that histone hyperacetylation in irradiated skin was visually evident deep in the subcutaneous layer at 6 hours after drug treatment (i.e., coincident with the peak of the drug concentration in the skin test) (FIGS. 1A, and 1C-1F). The acetylated H3 in the nuclei was used as a marker indicating the extent of drug penetration.

Example 3

Histone Deacetylase Inhibitors are Effective for Reducing Acute Radiation-Induced Normal Tissue Damage Adult female Sprague Dawley (SD) rats were purchased from the animal center of the National Science Council of Taiwan, and weighed 250-300 g at the time of irradiation. Each rat was caged alone and allowed chow and water. They were anesthetized with pentobarbital 50 mg/kg i.p. before irradiation. The skin over gluteal area was shaved completely and radiation fields with 2-cm diameter were outlined with a marking pen just prior to irradiation. An electron beam with 6 MeV energy produced by a linear accelerator was used. The dose was delivered on Day 0 at 4 Gy/min up to 40 Gy to the prepared area. Each group treated with a histone deacetylase inhibitor was further divided into three subgroups animals (5 each): one subgroup treated with skin irradiation followed by vehicle, another with skin irradiation followed by a histone deacetylase inhibitor, and the third with skin irradiation only. Then vaseline (negative control), madecassol ointment (positive control), or either vehicles or the 1% phenylbutyrate cream, 1% valproic acid cream, or 0.1% trichostatin A ointment were applied topically to the irradiated skin twice daily from Day 1 to Day 90 after irradiation. The mean dosage for each treatment in the respective groups was 16 mg vaseline per $cm^2$ skin, 16 mg madecassol per $cm^2$ skin, 50 mg phenylbutyrate per $cm^2$ skin, 50 mg valproic acid per $cm_2$ skin, 5 mg trichostatin A per $cm^2$ skin, and an equivalent amount of the vehicle base for the control groups. The gross skin reactions were evaluated in all rats. Acute skin reactions were evaluated and scored every other day until the 90th day after irradiation using the modified skin score system (Abe Y. and Urano M. Fraction size-dependent acute skin reaction of mice after multiple twice-a-day doses. International Journal of Radiation Oncology, Biology, Physics. 18(2):359-64, 1990): 0=normal, 0.5=slight epilation, 1.0=epilation in about 50% of the radiated area, 1.5=epilation in greater than 50% of the area, 2.0=complete epilation, 2.5=complete epilation with definitive edema or dry desquamation in more than 50% of the area, 3.0=moist desquamation in a small area, 3.5=moist desquamation in most of the area.

Figure 2:
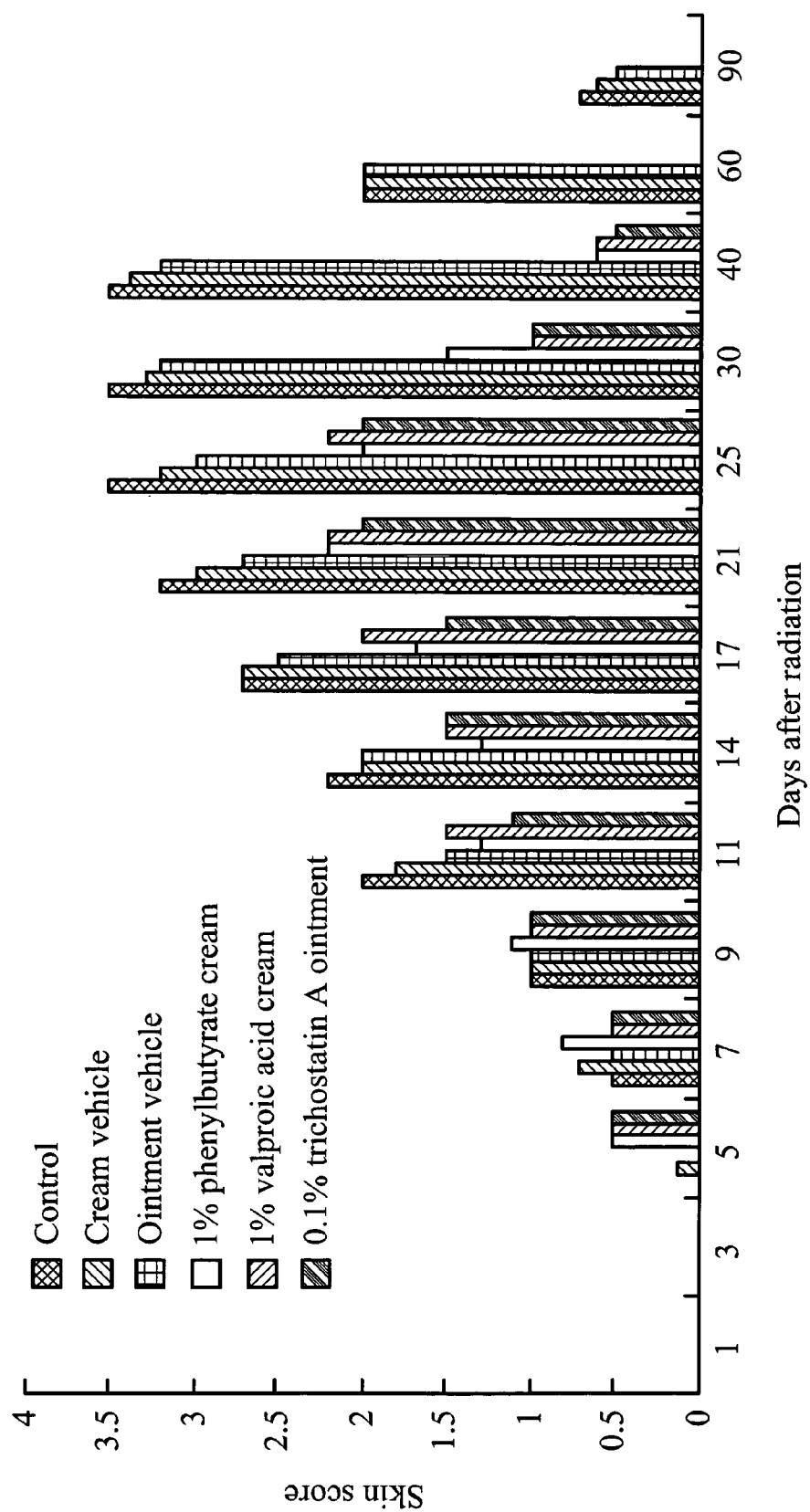
FIG. 2 is an acute skin reaction score diagram showing the time-course of the average skin score after 40Gy irradiation.

The skin score increases with more severe skin reaction. The average skin reaction scores in each group are shown in FIG. 2. On Day 11, the skin reactions in the groups treated with madecassol (positive control) or histone deacetylase inhibitors were less marked than those in the negative or vehicle control groups. By day 21, the epilation in the negative or vehicle groups had progressed to wet desquamation in most areas whereas in the madecassol or histone deacetylase inhibitor groups, it improved, and epithelium healing had begun quickly.

Example 4

Figures 3D, 3E, 3F:
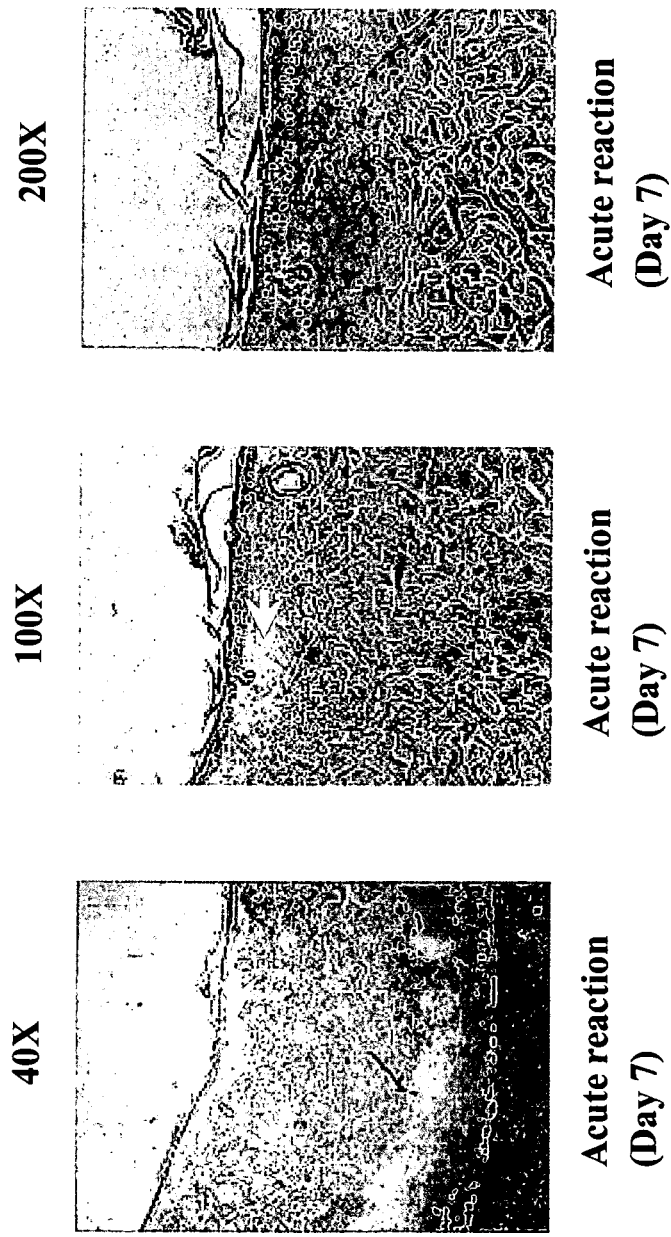
Figures 3J, 3K, 3L:
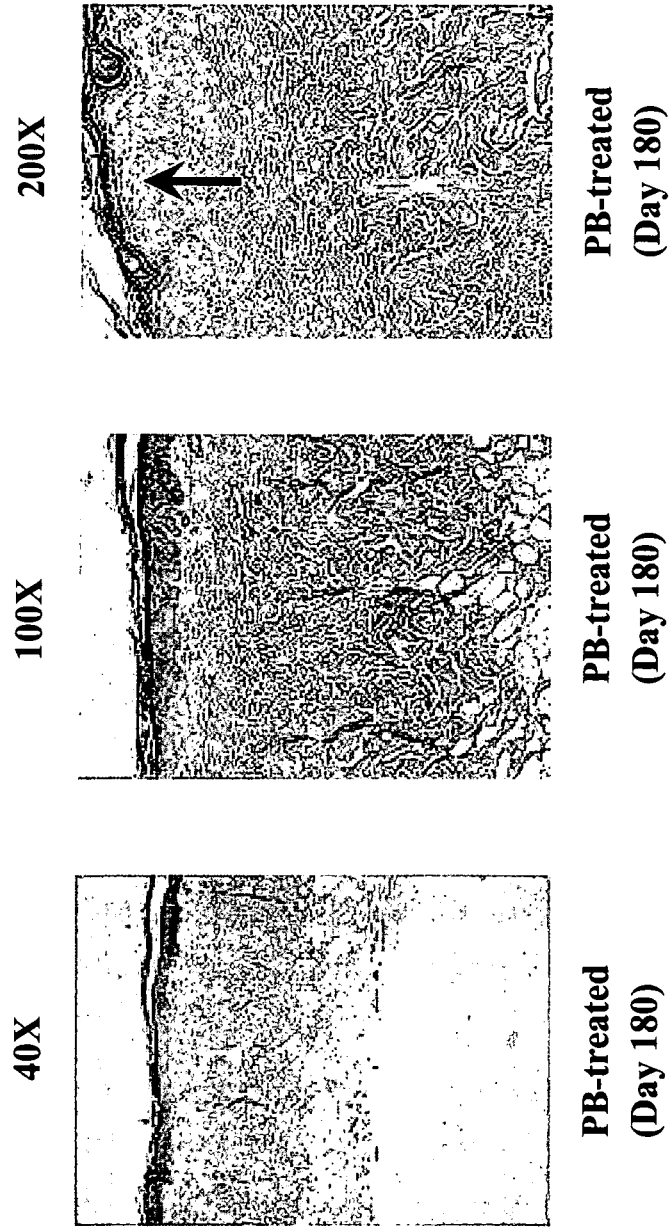
Figure 4A:
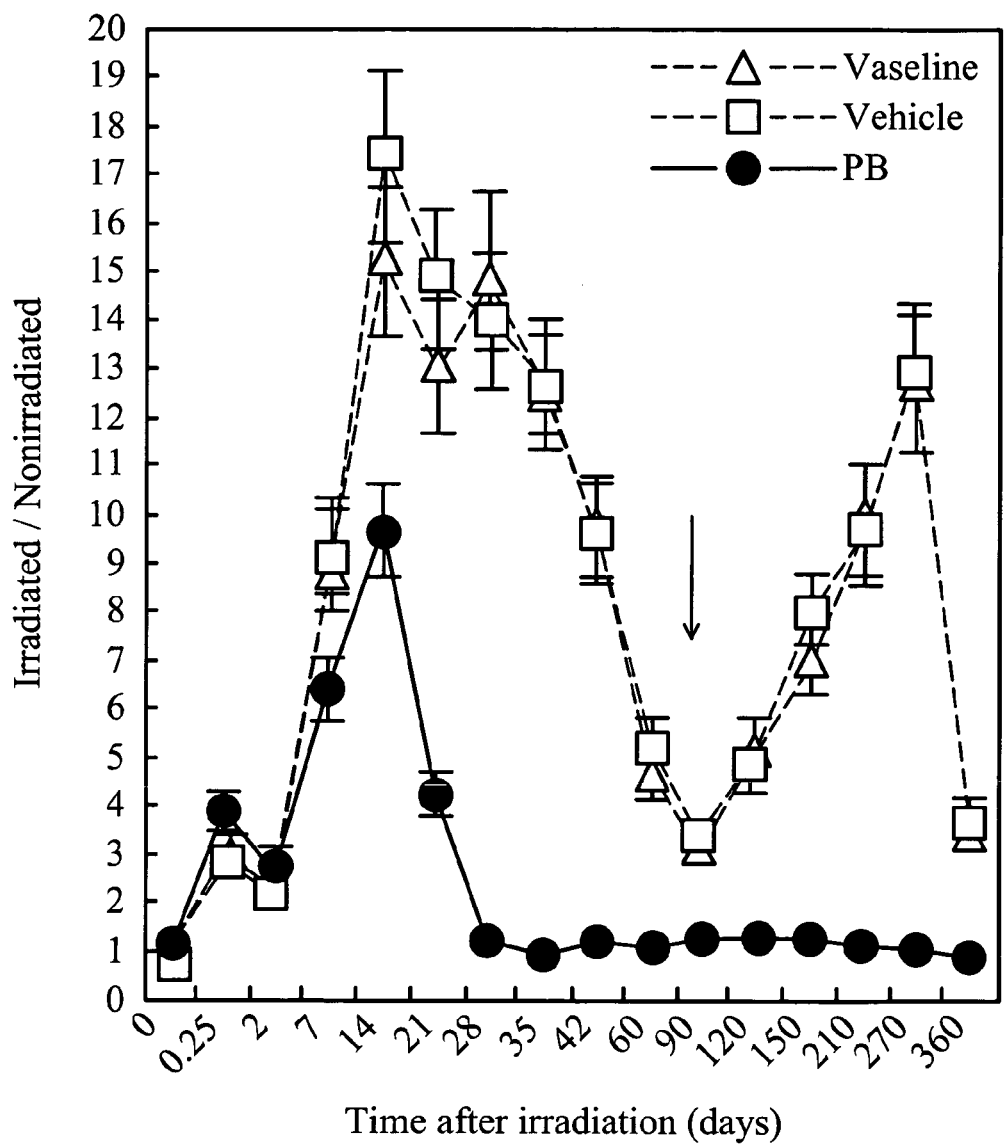
FIGS. 4A-4D shows the expression levels of TGF-β and TNF-α after irradiation treated with or without the topical HDAC inhibitor. Temporal variation in mRNA levels of TGF-β1, TGF-β2, TGF-β3, and TNF-α in skin after irradiation is normalized to the internal control GAPDH and expressed as a ratio to levels in nonirradiated control samples. Each point represents the mean of mRNA levels of 5 samples in the same group of Vaseline, vehicle, or phenylbutyrate (PB). The arrow indicates that the drug treatment was discontinued after Day 90 (*p<0.05, **p<0.001 in comparison with the PB-treated and vehicle groups).
Figure 4B:
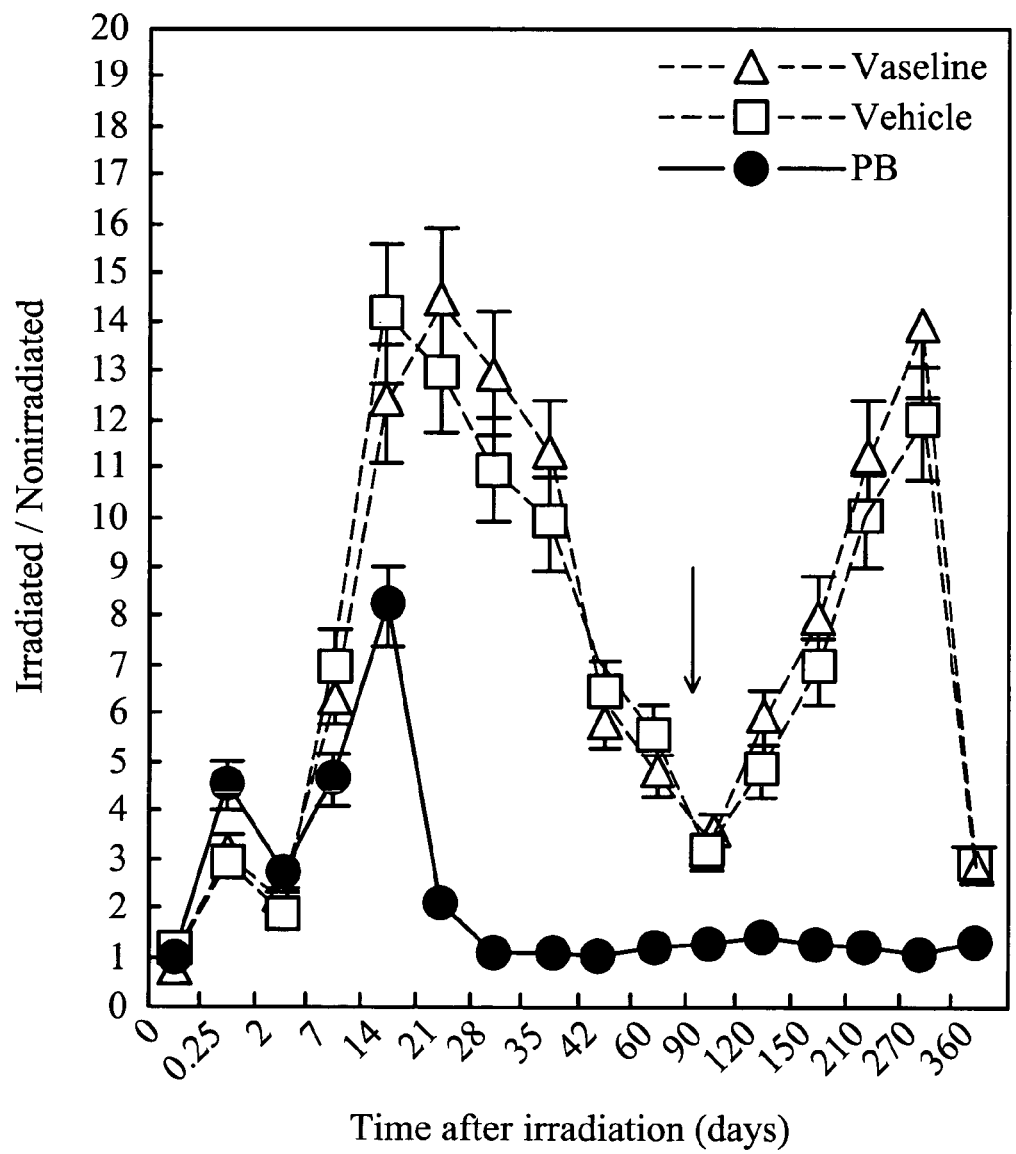
Figure 4C:
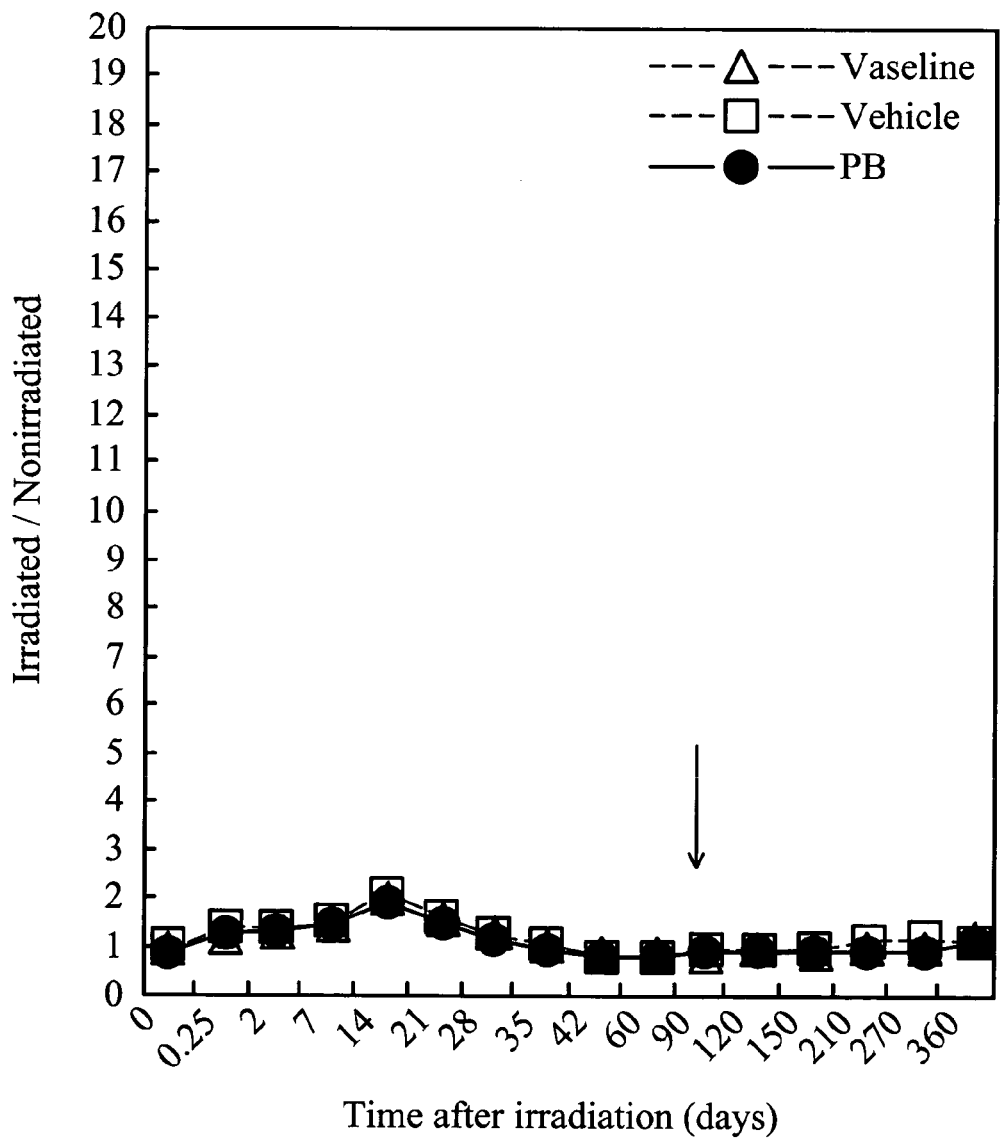
Figure 4D:
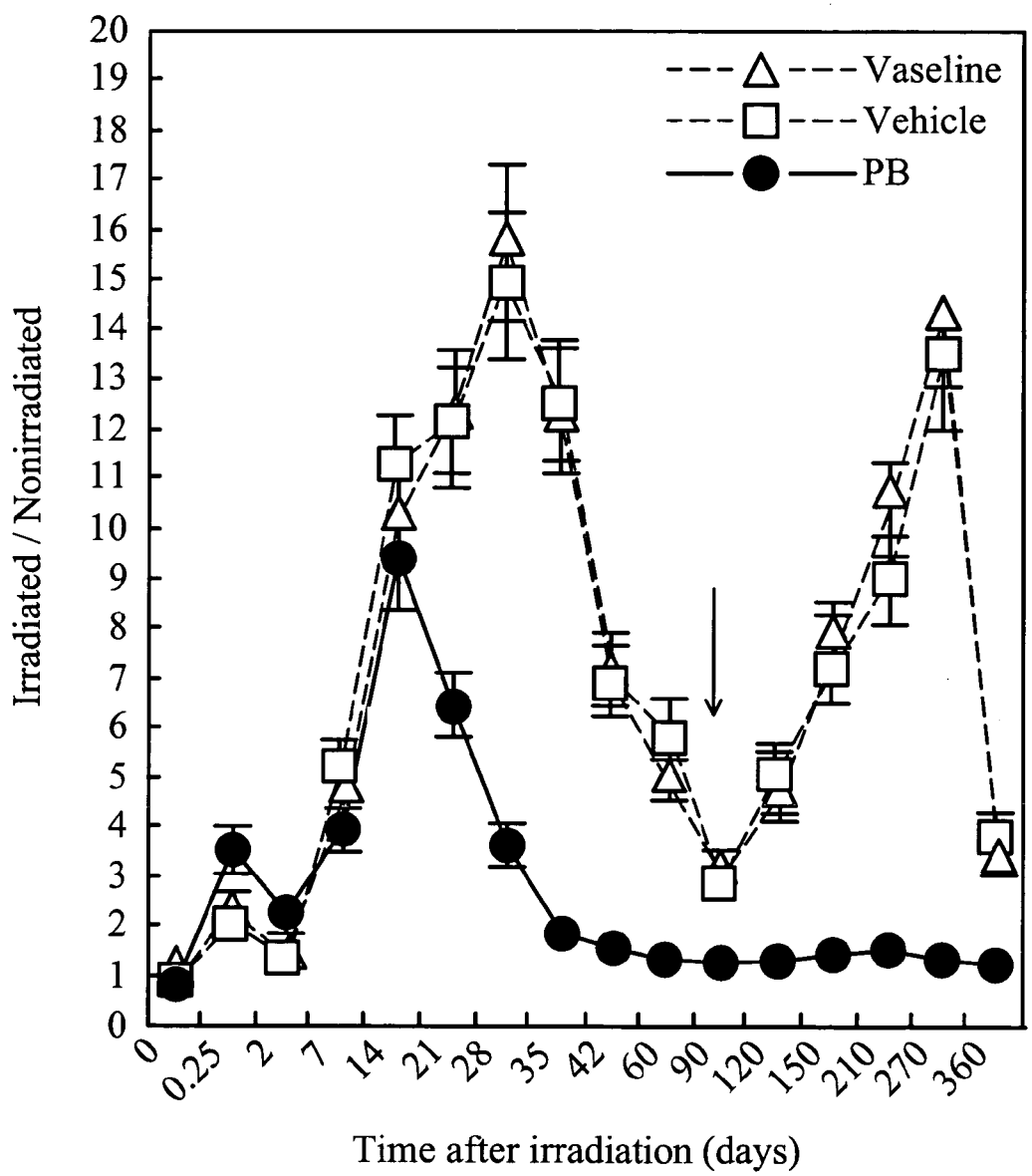
Figure 6A:
FIGS. 6A-6D are photographs of immunohistochemistry with the anti-TNF-α antibody showing that the expression of TNF-α, a proinflammatory cytokine, was suppressed by the histone deacetylase inhibitor.
Figure 6B:
Figure 6C:
Figure 6D:
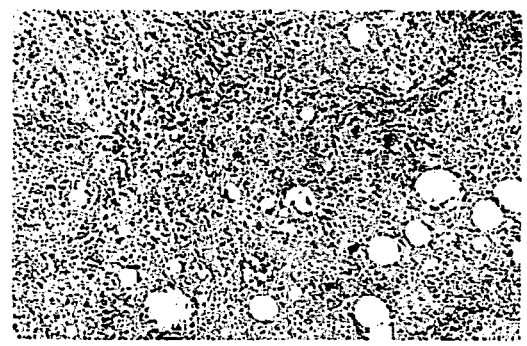

H&E Histology of Irradiated Skin Correlates with the Promotion of Wound Healing by the HDAC Inhibitor Valproic acid, trichostatin A, and phenylbutyrate are structurally unrelated histone deacetylase inhibitors, and all have similar effects on suppressing the radiation-induced skin damage including acute dermatitis and desquamation, and late fibrosis, ulceration and necrosis. As shown in FIG. 3, the groups treated with histone deacetylase inhibitors for 180 days have thicker epidermis with more cell layers but have thinner dermis (measured from epidermis to the subcutaneous fat layer) with less collagen deposition when compared to the vehicle group on Day 180 and the control groups (normal skin and acute reaction on Day 7).

Example 5

Changes in Radiation-Induced Histology after Treatment with the HDAC Inhibitor Correlate with the Suppression in Inflammatory and Fibrogenic Cytokine Expressions Because the development of radiation-induced damage has been attributed to radiation-induced temporal changes and the persistent up-regulation of proinflammatory cytokines such as TNF-α and fibrogenic growth factors such as TGF-β1 and P2, the suppression of radiation-induced damage by the HDAC inhibitor is shown to correlate with the suppression of TNF-α and TGF-β expression.

The timing of the peak appearance of TGF-β1, TGF-β2, and TNF-α expression levels induced by radiation correlated with the beginning of development of radiation-induced damage (FIG. 4). Levels of TGF-β1, TGF-β2, TGF-β3, and TNF-α mRNA were assessed using a multiple cytokine RNase protection assay kit (Riboquant; Pharmingen, San Diego, Calif.) that contained a template set to allow for the generation of a 32P-labeled antisense RNA probe set that hybridized with the target mRNA for TGF-β1, TGF-β2, TGF-β3, TNF-α, and internal control GAPDH. After hybridization of labeled probe to target RNA, unprotected RNA was digested by a ribonuclease (RNase), and protected RNA fragments were resolved on a 6% polyacrylamide gel and recorded by phosphorimaging (Molecular Dynamics Corp., Sunnyvale, Calif.). Densitometry was used to quantify the amount of each mRNA species and was normalized to the internal control GAPDH.

The means of skin scores for skin reactions from five rats in each group were calculated. The average levels of cytokine/growth factor mRNA from three skin samples in each group were normalized to the internal control GAPDH and expressed as a ratio to the average level in time-matched control groups. The Mann-Whitney test (Stata Statistical Software, College Station, Tex.) was used to determine statistical significance at the $p<0.05$ level for differences in average skin scores and in average mRNA levels, respectively, between treated and control rats.

In the phenylbutyrate (PB)-treated group, the highest surge of TGF-β1, TGF-β2, and TNF-α appeared at 6 hours after irradiation, but levels were subsequently suppressed after Day 14. The suppression still persisted at 12 months, even when topical PB treatment was discontinued at Day 90. In the Vaseline and vehicle control groups, mRNA levels of TGF-β1, TGF-β2, and TNF-α in the irradiated skin increased and fluctuated above the non-irradiated control levels over a period of 1 year and reached the first peak of 2-3-fold above the non-irradiated control levels at 6 hours after irradiation, the second peak of 10.5-16-fold around 14-28 days after irradiation, and the third peak of 13-14-fold at 9 months after irradiation; levels then declined to 2-3-fold normal levels by 12 months after irradiation. Although the mRNA levels of TGF-β1, TGF-β2, and TNF-α at the first peak at 6 hours in the PB group were higher than those in the Vaseline and vehicle control groups, they decreased to the levels lower than those in the Vaseline and vehicle groups at Day 14 and returned to the non-irradiated control levels at Day 28-35.

TGF-β1 and TGF-β2 have similar cellular effects in inhibiting epithelial cell growth and promoting dermal fibroblast proliferation, but TGF-β3 has the opposite effect. The level change of TGF-β3 mRNA was found that it exhibited a slightly transient increase of 2-fold in all irradiated groups at 14 days then progressively decrease to the non-irradiated control level or lower. No significant differences in TGF-β3 mRNA levels were observed between the irradiated groups treated with Vaseline, vehicle, or PB.

Example 6

Immunofluorescence of TGF-Beta, a Fibrogenic Growth Factor, in Irradiated Skin is Suppressed by the Histone Deacetylase Inhibitor The same pathological sections in example 4 were subjected to immunofluorescence with the anti-TGF-beta1,2 antibodies. As shown in FIG. 5, the TGF-beta protein, a strong fibrogenic factor, was up-regulated by irradiation, and highly expressed in fibrogenic skin both in keratinocytes of the epidermis and in myofibroblasts of the dermis on Day 7 and Day 180 in the acute reaction and vehicle-treated group, respectively, but the expression of TGF-beta was suppressed effectively in the PB-treated group on Day 180.

Example 7

Immunohistochemistry of TNF-Alpha, a Proinflammatory Cytokine, in Irradiated Skin is Suppressed by the Histone Deacetylase Inhibitor On Day 270, three of five rats in the Vaseline-treated group and four of five rats in the vehicle-treated group, compared with zero of five rats in the PB-treated group, showed chronic ulceration, necrosis, bullae formation, and inflammatory cell infiltration. The decrease in late radiation-induced skin damage by topical PB was consistent with the suppression of TNF-α expression (FIG. 6).

Example 8

Figure 7:
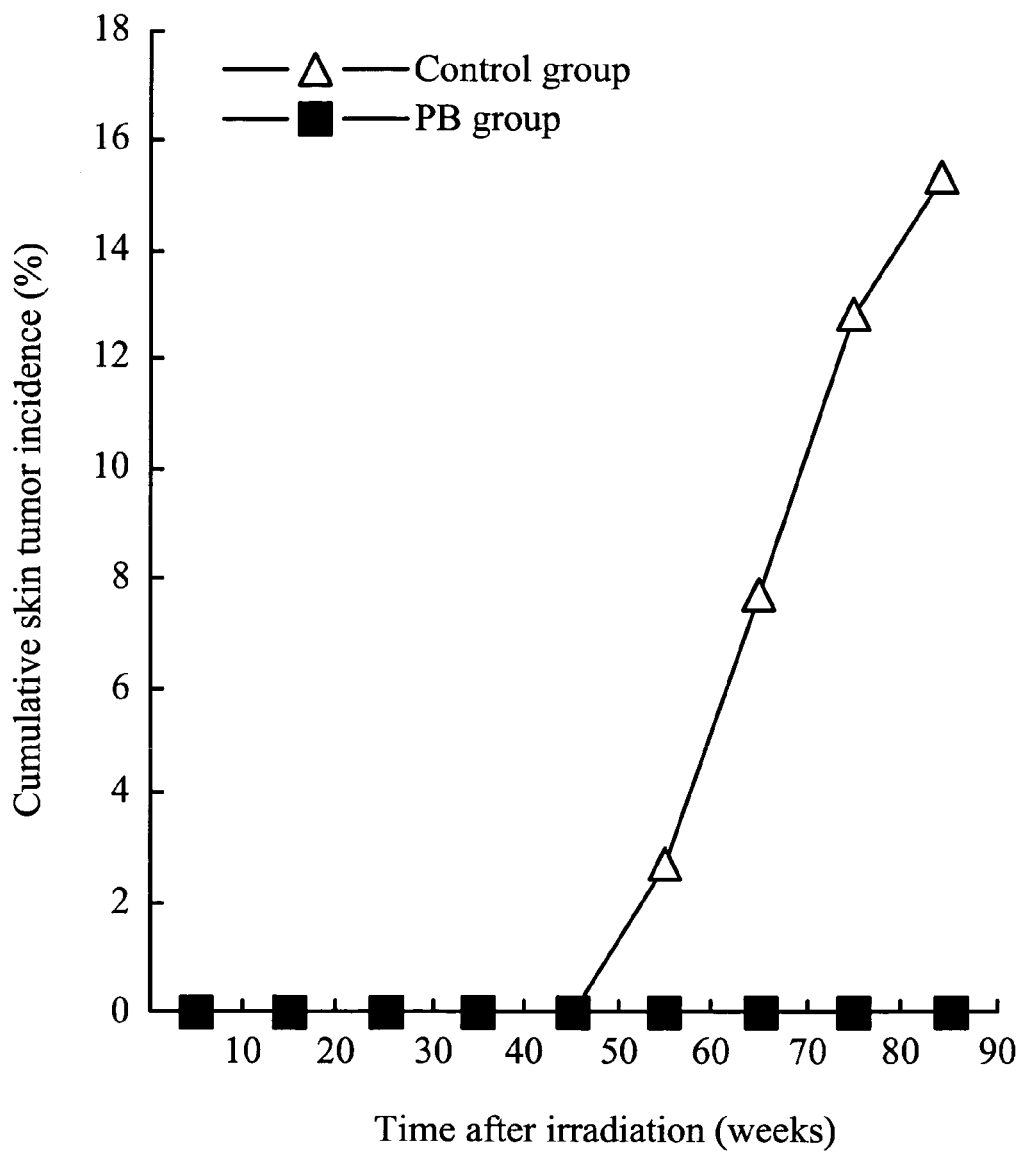
FIG. 7 shows the suppression of skin tumorigenesis after irradiation by the HDAC inhibitor. Newly developed skin or cutaneous tumors increased with time following radiation after 50 weeks in the control group that did not receive PB treatment, but no tumors developed in the PB-treated group.

Topical Phenylbutyrate (PB) Treatment Prevents Late Radiation-Induced Skin Tumor Formation Many studies have demonstrated that the chronic overexpression of TGF-β stimulates neoplastic growth. The decrease of TGF-β expression caused by PB treatment might decrease the incidence of late radiation-induced tumorigenesis. Newly developed skin or cutaneous tumors were found to increase with time after 50 weeks in the irradiated control group that did not receive PB treatment, but no tumors were seen in the PB-treated irradiated group (FIG. 7). At 90 weeks, a cumulative tumor incident of 15% (6 of 39) was observed in the irradiated group without PB treatment, compared with 0% (0 of 42) in the irradiated groups with PB treatment. The histology of radiation-induced tumors included fibroma, spindle cell sarcoma, basal cell carcinoma, and squamous cell carcinoma.

Example 9

Topical Phenylbutyrate (PB) Exhibits a Direct Antitumor Effect on Cutaneous Tumor Growth The syngeneic carcinoma cells 1MEA7R. 1 and CT-26 (purchased from American Type Culture Collection, Manassas, Va.) were subcutaneously injected into the flank areas of female BALB/c mice. The tumor was allowed to a maximum dimension of 0.5 cm. Topical HDAC inhibitors or vehicle was applied at a dose of 200 mg/mouse to cover the whole tumor surface and surrounding skin twice per day for 4 weeks. The tumor size was calculated weekly with a caliper according to the formula ab2/2, where a and b are the larger and smaller diameters (in centimeters), respectively.

Figure 8A:
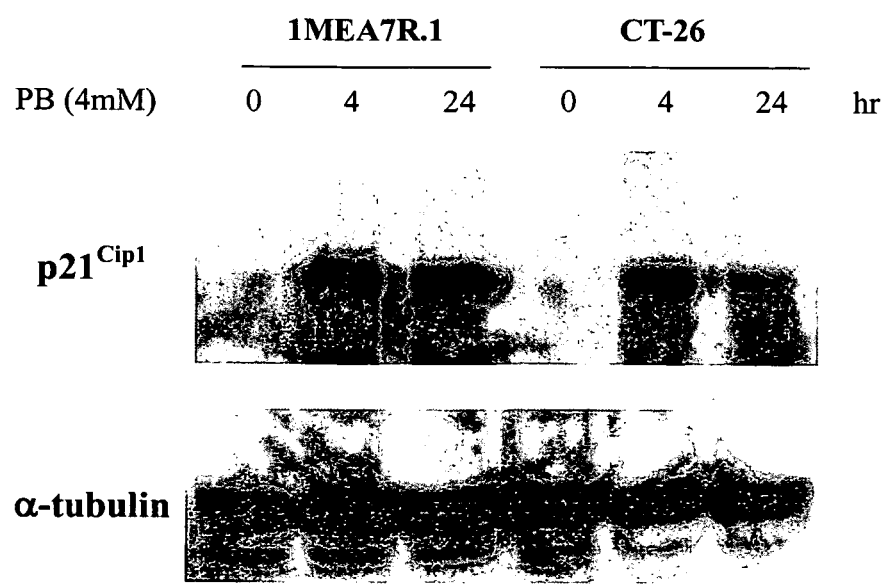
FIGS. 8A-8F show that the topical phenylbutyrate (PB) directly inhibits tumor growth.
Figure 8B:
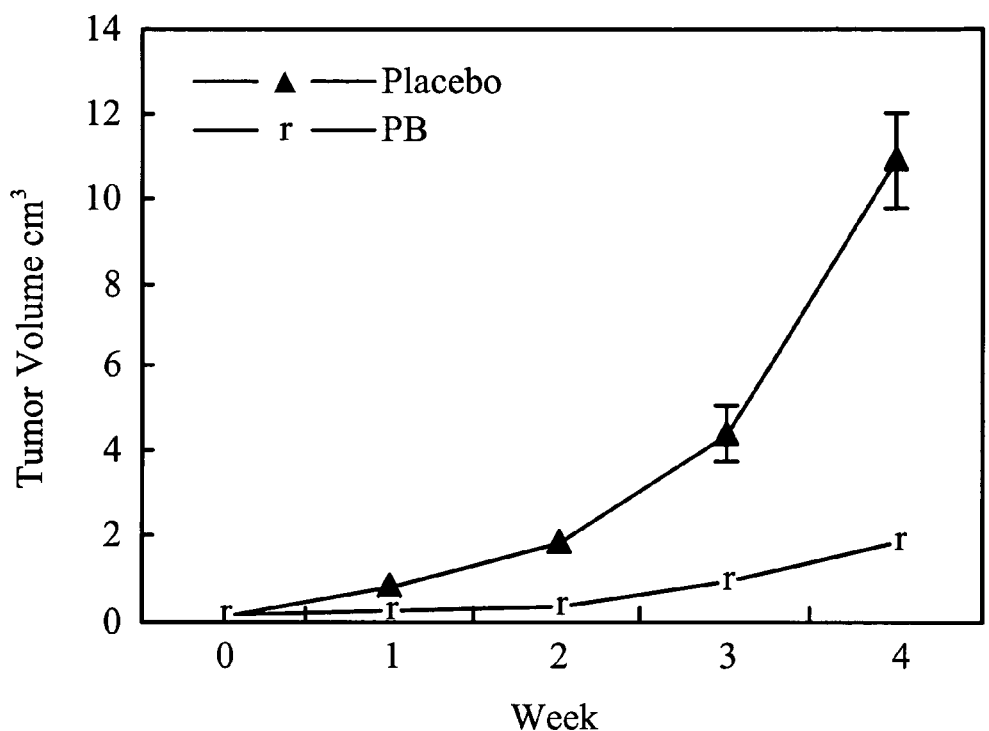
Figure 8C:
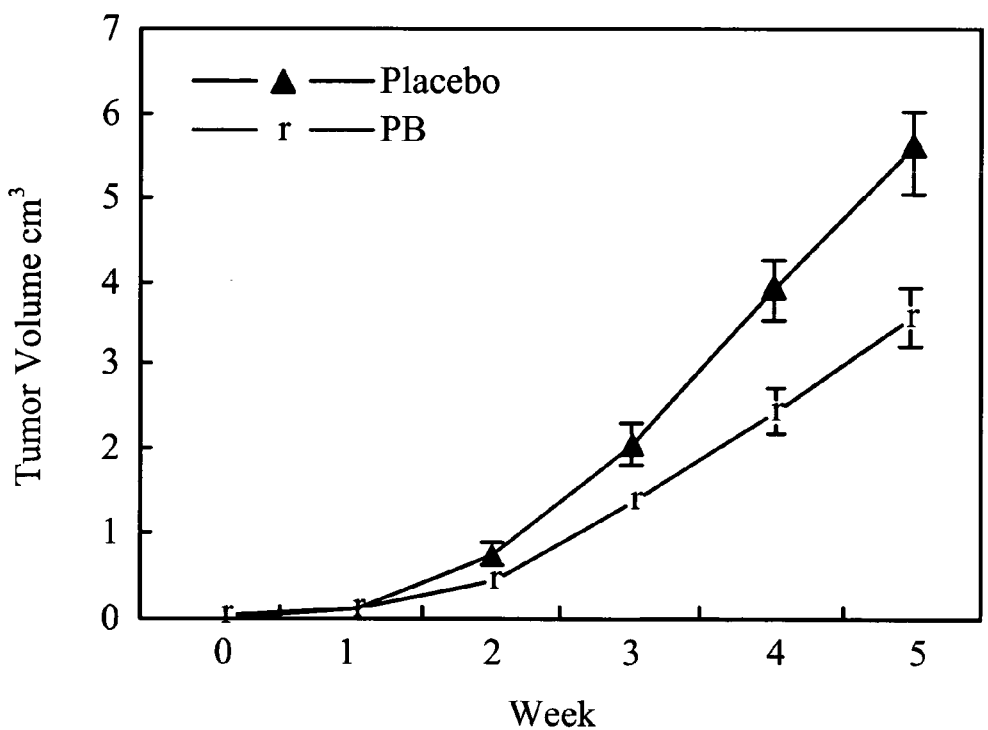
Figure 8D:
Figure 8E:
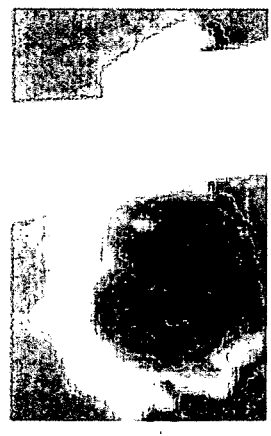
Figure 8F:

The topical PB formulation was show to have antitumor effects. BNL 1MEA7R.1 and CT-26 carcinoma cells, which showed growth inhibition by PB in vitro by the up-regulation of p21Cip1 (FIG. 8A), were inoculated into the back of syngeneic mice. Cutaneous tumors were allowed to grow to the largest dimension 0.5 cm (FIG. 8D), and PB was topically applied to the tumor surface at 200 mg/mouse twice per day. By 4 weeks, the tumor sizes of 1MEA7R.1 and CT-26 carcinomas in the placebo groups were almost 6- and 1.6-fold larger than those in the PB-treated groups, respectively (FIGS. 8B-8C). Cutaneous tumors in the PB-treated groups grew slowly without skin ulceration (FIG. 8F), whereas tumors in the control or placebo group grew rapidly and showed a necrotic appearance and skin ulceration (FIG. 8E). After 5 weeks of treatment, withdrawal of topical PB resulted in a loss of tumor growth inhibition, and these tumors then reached the same size as those in the control or placebo groups within 2 weeks.

Example 10

Figure 9:
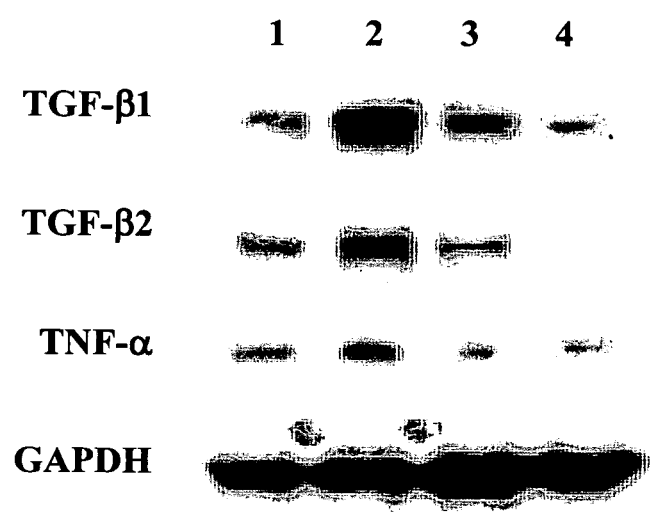
FIG. 9 is a northern blot assay showing that the up-regulation of TGF-β1, 2, and TNF-α expression in skin after irradiation is suppressed by structurally unrelated HDAC inhibitors (trichostatin A and valproic acid).

Similar Effects of Structurally Unrelated Antitumor HDAC Inhibitors in Treating Radiation-Induced Normal Tissue Damage and in Preventing Late Radiation-Induced Tumorigenesis In addition to PB, other structurally unrelated antitumor HDAC inhibitors, such as trichostatin A (an antifungal agent) and valproic acid (an antiseizure agent), also ameliorated the development of radiation-induced damage and tumorigenesis and decreased the radiation-induced TGF-β1, TGF-β2, and TNF-α expression (FIG. 9 and Table 3).

Total RNA was isolated from frozen skin samples using Trigent (Molecular Research Center Inc., Cincinnati, Ohio). Total RNA (30 µg) was electrophoresed in a denaturing formaldehyde-agarose gel, blotted onto Hybond N (Amersham, Amersham, UK), and fixed by ultraviolet (UV) irradiation. The membrane was incubated with 32P-labeled probes, as described below, in Rapid-hyb buffer (Amersham). To prepare probes for rat TGF-β1 and TGF-β2, their full-length coding sequences were amplified by reverse-transcription polymerase chain reaction using specific forward (TGF-β1, 5'-CGGGTGGCAGGCGAGAGC-3' (SEQ ID NO:1) and TGF-β2,5'-CATGCACTACTGTGTGCT-3' (SEQ ID NO:2)) and reverse (TGF-β1,5'-GGAATTGTTGCTATATTTCTGC-3' (SEQ ID NO:3) and TGF-β2,5'-CCGAGGACTTTAGCT-GCA-3' (SEQ ID NO:4)) primers. A template set of TNF-α and GAPDH from the RNase protection assay kit (Riboquant; Pharmingen) was used to generate 32P-labeled antisense RNA probes that hybridized with the mRNA for TNF-α and GAPDH.

TABLE 3

Summary of histological findings in irradiated skin treated with different HDAC inhibitors

| Treatment group | Irradiated skin reaction | | | | | | | | | Antitumor effect Week 90 | |
|---|---|---|---|---|---|---|---|---|---|---|---|
| | Day 1-90 | | | Day 90-180 | | | Day 180-360 | | | | |
| | A | B | C | D | E | F | G | H | I | J | K |
| Vaseline | +++++ | +++++ | +++ | +++++ | | | +++++ | +++ | | No | No |
| Madecassol | +++++ | ++ | | +++++ | | + | ++++ | + | + | No | No |
| Cream vehicle | +++++ | +++++ | +++ | +++++ | | | +++++ | ++++ | | No | No |
| Ointment vehicle | +++++ | +++++ | +++ | +++++ | | | +++++ | +++ | | No | No |
| 1% phenylbutyrate cream | +++++ | ++ | | | +++++ | +++++ | | | +++++ | yes | ++++ |
| 1% valproic acid cream | +++++ | ++ | | | +++++ | +++++ | | | +++++ | yes | +++ |
| 0.1% trichostatin A ointment | +++++ | ++ | | | +++++ | +++++ | | | +++++ | yes | ++++ |

The histological findings on skin specimens from 5 irradiated rats in each group are represented as follows: A, subepithelial swelling. B, dry desquamation in more than 50% of the area. C, wet desquamation in more than 50% of the area. D, atrophy of epidermis in most areas. E, atrophy of skin appendages in most areas. F, increased thickness of epithelium with more cell layers. G, increased collagen deposition, more vessel density, and increased thickness of dermis. H, chronic ulceration, necrosis, bullae formation, and more inflammatory cell infiltrate. I, down-regulation of TGF-β1, 2, and TNF-α. J, prevention of late radiation-induced tumorigenesis. K, Demonstration of direct antitumor effect on cutaneous tumor growth. The "+" to "+++++" means specimens from one to five rats showed the reaction or effect as indicated.

Example 11

Valproic Acid Enhances Tumor Radiosensitization

Radiation enhancement ratio (RER) is used to calculate the ratio of radiation doses that give the same effect. RER=(Radiation dose without drug treatment at 10% survival fraction)/(Radiation dose with drug treatment at 10% survival fraction).

Figure 10:
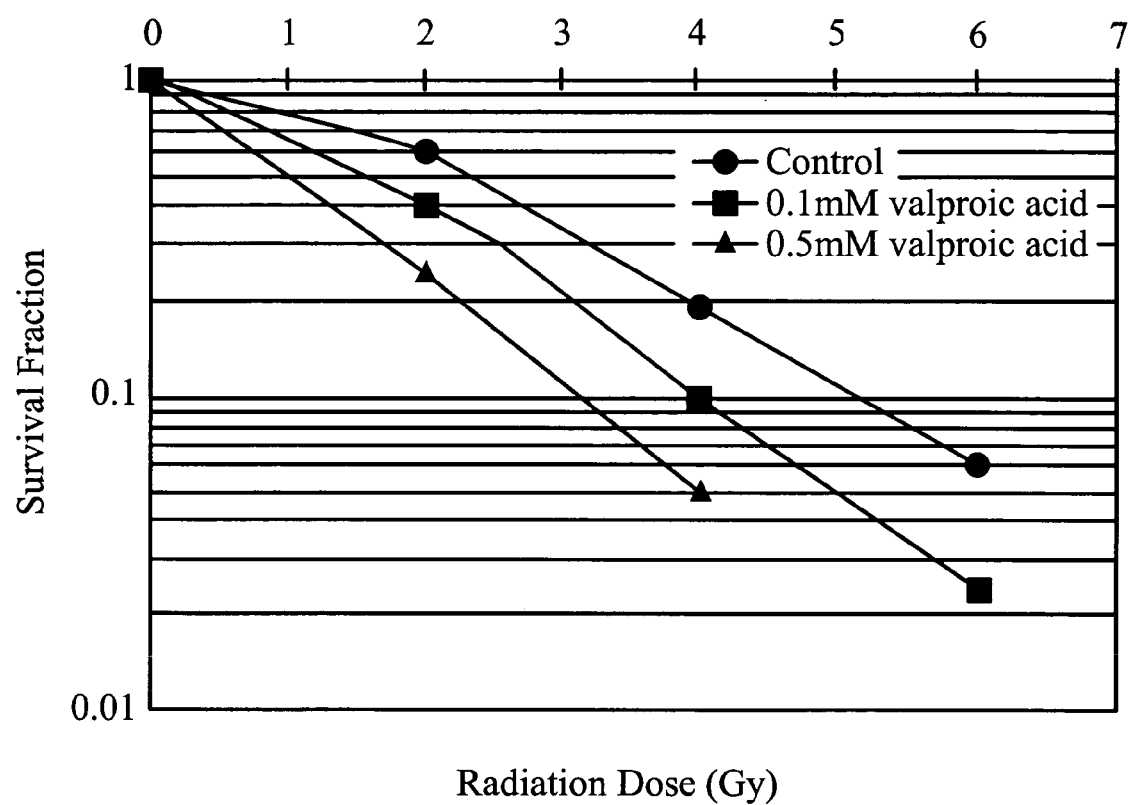
FIG. 10 shows enhancement of tumor radiosensitization by Valproic acid. Points represent the mean of two different experiments performed in triplicate; SD less than 10%.

Valproic acid (0.1 mM or 0.5 mM) was added in CNE2 nasopharyngeal carcinoma cells 60 minutes prior to radiation with radiation dose from 2 to 16 Gy, then washed out. After one week, colonies containing more than 50 cells were counted. The plating efficiency was the same in control and in PB-treated group. Radiation enhancement ratio (RER) of 0.1 mM or 0.5 mM valproic acid was increased at 10% survival up to 1.2 and 1.7, respectively (FIG. 10).

Example 12

Co-Administration of Trichostatin a (TSA), Ganciclovir (GCV), and Radiation (RT) Selectively Kill the Epstein-Barr Virus (EBV)-Infected Carcinoma Cells HDAC inhibitor as a gene modulator may up-regulate EBV thimidine kinase activity to render EBV-associated tumor killing by ganciclovir (GCV), which can be phosphorylated by EBV thymidine kinase to inhibit cellular DNA polymerase to cause cell death in S phase of cell cycle. Because HDAC inhibitor also acts as an antiproliferative agent and radiosensitizer, the combination therapies of TSA, GCV and radiation (RT) may have therapeutic benefits on EBV-associated tumors such as nasopharyngeal carcinoma, Hodgkin's lymphoma, X-linked lymphoproliferative disease, AIDS-related non-Hodgkin's lymphoma, and smooth muscle tumors in immunosuppressed children.

For EBV thimidine kinase activity assay, an equal amount of cytosol fraction was incubated with reaction buffer (50 mM Tris-HCl pH 7.4, 1 mg/ml BSA, 3 mM creatine phosphate, 11.2 U/ml creatine phosphokinase, 0.1 μm [3H-8]-GCV (specific activity 13.5 Ci/mmol), 2.5 mM ATP, 2.5 mM $MgCl_2$, 10 mM NaF, 10 mM DTT) at 37° C. for 30 mins. The reaction mixtures were added on WhatmanR DE-81 ion exchange chromatography papers, which were then washed with 1.5 mM NH4COOH three times to remove unphosphorylated form of [3H-8]-GCV. After air dry, these papers were incubated with liquid scintillation cocktail overnight. The phosphorylation form of [3H-8]-GCV bound on WhatmanR DE-81 ion exchange chromatography paper was measured by LS6500 scintillation counter (Beckman).

Figure 11A:
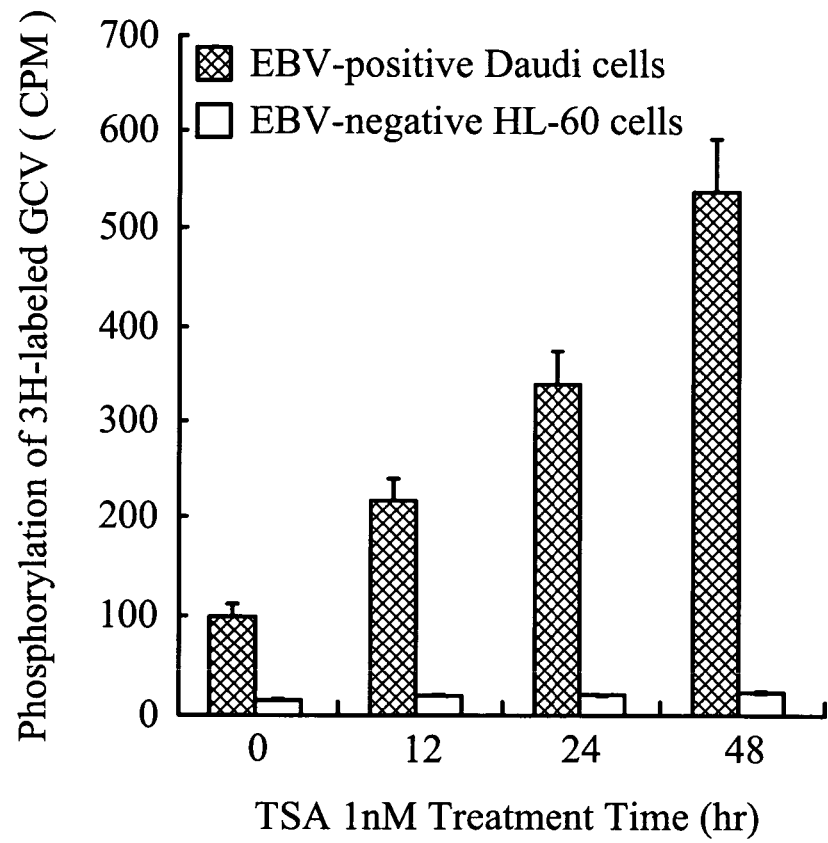
FIGS. 11A-11B show that Epstein-Barr virus (EBV)-positive Daudi's lymphoma cells were selectively destroyed but EBV-negative HL-60 leukemia cells were not by the low dose of combination of HDAC inhibitor, antibiotic and radiation.
Figure 11B:
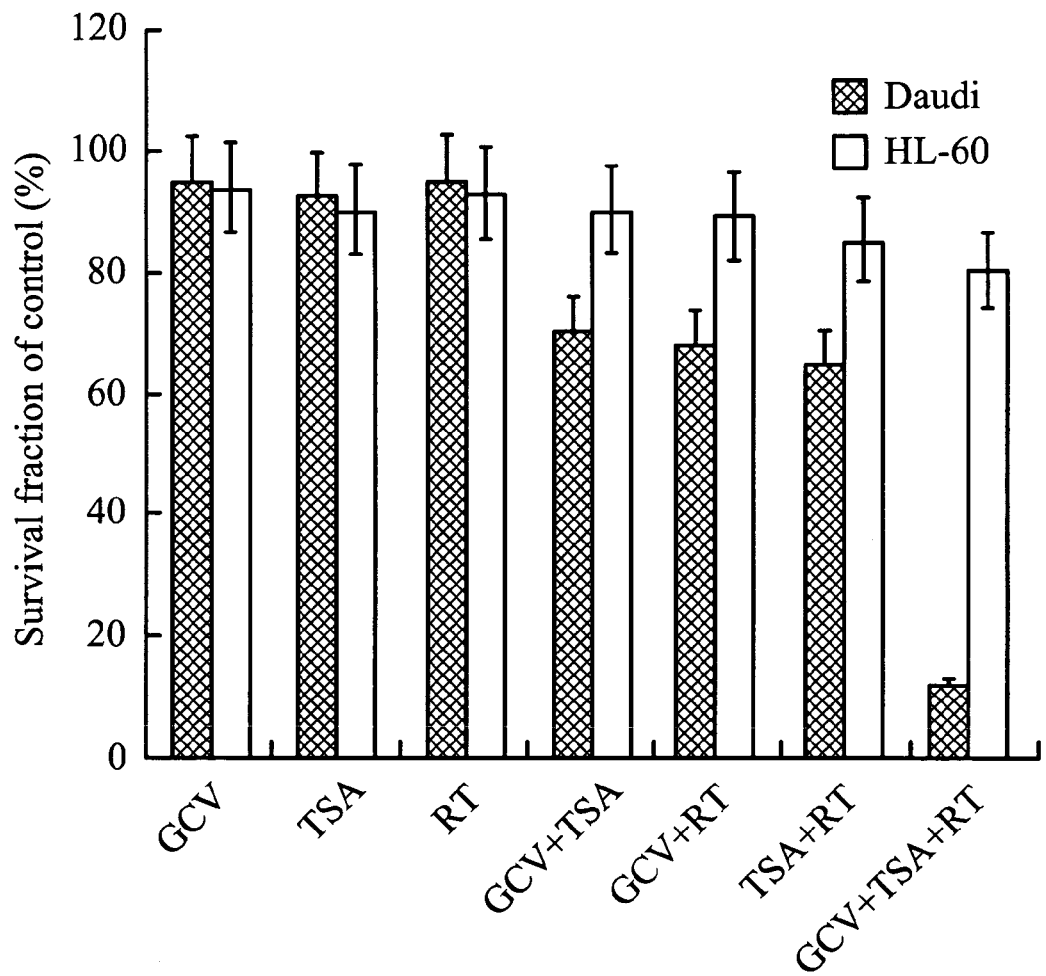

As shown in FIG. 11A, the EBV thymidine kinase activity was up-regulated by TSA 1 nM treatment for 48 hours. The combination of TSA, GCV and radiation produced selectively maximal death in EBV-positive cells but not in EBV-negative cells (FIG. 11B). Daudi cells (EBV+) and HL-60 (EBV−) were treated with ganciclovir (GCV) (10 μg/ml) and/or trichostatin A (TSA) (1 nM) for 48 hours, then radiated with or without 1 Gy radiation (RT). Viable cells were counted 1 week later.

Example 13

Animal Model of Treatment of Radiation-Induced Mucositis with Topical Phenylbutyrate Hamster models of chemotherapy-induced mucositis and radiation-induced mucositis have been developed. The reproducibility of the model has been validated, with the consistent appearance of ulcerative mucositis between days 12 and 15 following radiation. Using this model, the efficacies of topical phenylbutyrate gel and solution have been tested for their abilities to modify the course of radiation-induced mucositis. An acute radiation dose of 40 Gy on day 0 was administered in order to produce severe mucositis around day 15. The use of acute radiation to induce mucositis was preferable to the use of either fractionated radiation or chemotherapy for these initial studies. The acute model had little systemic toxicity, resulting in fewer animal deaths. This fact permitted the use of smaller groups in the initial studies. The acute model has been used successfully to demonstrate the presence or absence of efficacy for a large number of compounds. The acute radiation model is therefore appropriate as an initial protocol for screening diverse families of compounds.

Mucositis was induced using an acute radiation protocol. A single dose of radiation (40 Gy/dose) was administered to all animals on Day 0. Radiation was generated with a 250 kilo-volt potential (15 mA) source at a focal distance of 50 cm, hardened with a 0.35 mm Cu filtration system. Irradiation targeted the left buccal pouch mucosa at a rate of 121.5 cGy/minute. Prior to irradiation, animals were anesthetized with an intraperitoneal injection of sodium pentobarbital (80 mg/kg). The left buccal pouch was everted, fixed, and isolated using a lead shield.

This study used twenty hamsters that were randomly divided into four groups of five animals per group. Each group was assigned a different treatment as follows: Group 1 animals: 20 μPBS/hamster; Group 2 animals: 200 μg sodium phenylbutyrate/20 μl PBS/hamster; Group 3 animals: 20 mg placebo (gel base)/hamster; Group 4 animals: 20 mg phenylbutyrate gel/hamster. The substances were applied topically to the radiation-induced mucositis area of test hamsters once daily for 10 consecutive days since Day 15. The mucositis wound area, traced onto the clear plastic sheets on Day 15, 17, 19, 21, 23, and 25, were quantitated by use of an Image Analyzer (Life Science Resources VISTA, Version 30). The mucositis wound area half-closure time (CT50) was determined by linear regression using GraphPad Prism (Graph Pad Software USA) and unpaired Student's t test was applied for comparison between treated and placebo group at each measurement time point. Differences were considered statistically significant at $p<0.05$.

As shown in Table 4, significant increase ($p<0.01$) in mucositis wound closure was observed in Group 2 (200 μg sodium phenylbutyrate/20 μl PBS/hamster) on Day 21, 23 and 25, and in Group 4 (20 mg phenylbutyrate gel/hamster) on Day 17, 19, 21, 23 and 25. CT50 was also significantly reduced ($p<0.01$) to 6.5±0.2 days in Group 2 (relative to 7.7±0.2 days in Group 1), and to 8.9±0.2 days in Group 4 (relative to 10.5±1.3 days in Group 3).

TABLE 4 mucositis wound healing treated with phenylbutyrate (PB)

| Group (5 hamsters each) | Treatment (topically applied × 10 daily since Day 15 after radiation) | Averaged (N = 5) closure of mucositis wound (%) | | | | | CT50 Days |
|---|---|---|---|---|---|---|---|
| | | Day 17 | Day 19 | Day 21 | Day 23 | Day 25 | |
| 1. (Solution control) | 20 μl PBS/hamster | 24.0 ± 3.0 | 42.6 ± 1.2 | 49.6 ± 1.7 | 57.6 ± 1.8 | 65.0 ± 2.5 | 7.7 ± 0.2 |
| 2. (PB solution) | 200 μg sodium phenylbutyrate/ 20 μl PBS/hamster | 28.2 ± 4.3 | 45.8 ± 2.9 | 57.4 ± 1.2** | 69.2 ± 1.4** | 74.8 ± 1.5** | 6.5 ± 0.2** |
| 3. (Gel control) | 20 mg placebo(gel base)/hamster | 9.0 ± 5.6 | 14.8 ± 6.0 | 34.8 ± 5.5 | 47.8 ± 5.3 | 54.4 ± 7.7 | 10.5 ± 1.3 |
| 4. (1% PB gel) | 20 mg phenylbutyrate gel/hamster | 26.3 ± 3.8* | 33.6 ± 2.0** | 40.8 ± 2.8** | 50.8 ± 2.8** | 58.2 ± 2.5** | 8.9 ± 0.2** |

Differences are considered significant at
*P < 0.05,
**P < 0.01.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally and functionally analogous to histone deacetylase inhibitors described above can also be used to practice the present invention. Thus, other embodiments are also within the claims.

What is claimed is:

1. A method for reducing radiation-induced normal tissue damage in a subject, comprising
identifying a subject that has radiation-induced normal tissue damage, and
administering a composition containing a histone deacetylase inhibitor wherein the inhibitor is sodium phenylbutyrate and a pharmaceutically acceptable carrier or a pharmaceutically acceptable salt thereof to the subject, wherein the radiation-induced normal tissue damage is desquamation, dermatitis, mucositis, epidermal atrophy, tissue necrosis, bulla formation, or plantar-palmar syndrome.

2. The method as claimed in claim 1, wherein the composition is administered non-orally.

3. The method as claimed in claim 1, wherein the composition is a cream, an ointment, a gel, a paste, a powder, a lotion, a patch, a suppository, a liposome formation, a suspension, a mouth wash, an enema, an injection solution, or a drip infusion.

4. The method as claimed in claim 1, wherein the histone deacetylase inhibitor is from 0.001% to 100% by weight of the composition.

5. The method of claim 1, wherein the radiation-induced normal tissue damage is desquamation, dermatitis, epidermal atrophy, tissue necrosis, bulla formation, or plantar-palmar syndrome.

* * * * *

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
cgggtggcag gcgagagc                                                 18

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
catgcactac tgtgtgct                                                 18

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ggaattgttg ctatatttct gc                                            22

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
ccgaggactt tagctgca                                                 18
```